(12) United States Patent
Stock et al.

(10) Patent No.: US 9,890,504 B2
(45) Date of Patent: Feb. 13, 2018

(54) SYSTEMS AND METHODS FOR SENSING WEAR OF REDUCING ELEMENTS OF A MATERIAL REDUCING MACHINE

(71) Applicants: Joseph D. Stock, Newton, IA (US); Ty Hartwick, Pella, OH (US); Robert D. Franz, Ottumwa, IA (US)

(72) Inventors: Joseph D. Stock, Newton, IA (US); Ty Hartwick, Pella, OH (US); Robert D. Franz, Ottumwa, IA (US)

(73) Assignee: Vermeer Manufacturing Company, Pella, IA (US)

( * ) Notice: Subject to any disclaimer, the term of this patent is extended or adjusted under 35 U.S.C. 154(b) by 41 days.

(21) Appl. No.: 14/651,951

(22) PCT Filed: Dec. 12, 2013

(86) PCT No.: PCT/US2013/074672
§ 371 (c)(1),
(2) Date: Jun. 12, 2015

(87) PCT Pub. No.: WO2014/093625
PCT Pub. Date: Jun. 19, 2014

(65) Prior Publication Data
US 2015/0322634 A1    Nov. 12, 2015

Related U.S. Application Data

(60) Provisional application No. 61/736,303, filed on Dec. 12, 2012.

(51) Int. Cl.
*E01C 23/088* (2006.01)
*E01C 23/12* (2006.01)
(Continued)

(52) U.S. Cl.
CPC .......... *E01C 23/127* (2013.01); *E01C 23/088* (2013.01); *E02F 3/20* (2013.01);
(Continued)

(58) Field of Classification Search
CPC ....... E21C 35/00; E01C 23/088; E01C 23/127
See application file for complete search history.

(56) References Cited

U.S. PATENT DOCUMENTS 3,990,805 A * 11/1976 Ducrohet .............. B23B 49/001
                                                        324/161
4,006,936 A    2/1977 Crabiel
(Continued)

FOREIGN PATENT DOCUMENTS

AT           382 683         3/1987
AU       2009212871 B2       3/2010
(Continued)

OTHER PUBLICATIONS

International Search Report for corresponding International Patent Application No. PCT/US2013/074672 dated Mar. 27, 2014.
(Continued)

*Primary Examiner* — John J Kreck
(74) *Attorney, Agent, or Firm* — Merchant & Gould P.C.

(57) ABSTRACT

The present disclosure relates generally to systems and methods for sensing wear in machines designed to reduce or break-down material. More particularly, the present disclosure relates to systems and methods for sensing wear of reducing elements used by excavation machines such as surface excavation machines. The present disclosure relates to a wear sensing system including a multilevel wear sensor protection system. The multi-level wear sensor protection system includes a first level of protection, a second level of protection, and a third level of protection.

16 Claims, 34 Drawing Sheets

(51) Int. Cl.

| | | |
|---|---|---|
| *E21C 27/24* | (2006.01) | |
| *E02F 9/26* | (2006.01) | |
| *E21C 35/00* | (2006.01) | |
| *G01N 3/56* | (2006.01) | |
| *E02F 3/20* | (2006.01) | |
| *E02F 5/08* | (2006.01) | |
| *E02F 5/14* | (2006.01) | |
| *E02F 9/28* | (2006.01) | |
| *E21B 3/00* | (2006.01) | |
| *E21B 12/02* | (2006.01) | |

(52) U.S. Cl.
CPC ............... *E02F 5/08* (2013.01); *E02F 5/145* (2013.01); *E02F 9/26* (2013.01); *E02F 9/264* (2013.01); *E02F 9/267* (2013.01); *E02F 9/2866* (2013.01); *E21B 12/02* (2013.01); *E21C 1/00* (2013.01); *E21C 27/24* (2013.01); *E21C 35/00* (2013.01); *G01N 3/56* (2013.01)

(56) References Cited

U.S. PATENT DOCUMENTS

| | | | |
|---|---|---|---|
| 4,176,396 A | | 11/1979 | Howatt |
| 4,181,360 A | | 1/1980 | Wilson |
| 4,591,784 A | | 5/1986 | Kolitsch et al. |
| 4,637,753 A | | 1/1987 | Swisher, Jr. |
| 4,845,763 A | | 7/1989 | Bandyopadhyay et al. |
| 5,875,980 A | | 3/1999 | Schmid |
| 6,201,567 B1 | * | 3/2001 | Kuroda ............... B23D 37/005 348/86 |
| 6,769,836 B2 | | 8/2004 | Lloyd |
| 6,990,390 B2 | | 1/2006 | Groth et al. |
| 7,066,555 B2 | | 6/2006 | Hansen et al. |
| 7,135,856 B2 | | 11/2006 | Eidenvall et al. |
| 7,470,082 B2 | | 12/2008 | Lloyd |
| 7,957,944 B2 | | 6/2011 | Herbst |
| 8,047,741 B2 | | 11/2011 | Von Schonebeck et al. |
| 8,122,798 B1 | | 2/2012 | Shafer et al. |
| 8,386,196 B2 | | 2/2013 | Wagner et al. |
| 2003/0127905 A1 | | 7/2003 | Haroldsen et al. |
| 2005/0207841 A1 | * | 9/2005 | Holl ...................... E01C 23/088 404/94 |
| 2008/0153402 A1 | | 6/2008 | Arcona et al. |
| 2008/0173740 A1 | | 7/2008 | Parker et al. |
| 2010/0063691 A1 | | 3/2010 | Hall et al. |
| 2010/0076697 A1 | | 3/2010 | Wagner et al. |
| 2010/0131234 A1 | | 5/2010 | Stewart et al. |
| 2010/0139975 A1 | | 6/2010 | Teodorescu et al. |
| 2010/0164951 A1 | | 7/2010 | Stewart |
| 2010/0251580 A1 | | 10/2010 | Quarfordt et al. |
| 2010/0301016 A1 | | 12/2010 | Luo et al. |
| 2011/0121633 A1 | | 5/2011 | Hall et al. |
| 2012/0175938 A1 | | 7/2012 | Arcona et al. |
| 2012/0217357 A1 | | 8/2012 | Franke |
| 2012/0256470 A1 | | 10/2012 | Von Schoenebeck et al. |
| 2014/0070598 A1 | * | 3/2014 | von Schoenebeck . E01C 23/088 299/10 |

FOREIGN PATENT DOCUMENTS

| | | |
|---|---|---|
| AU | 2013100451 | 5/2013 |
| CH | 541 713 | 9/1973 |
| DE | 2 349 827 A1 | 4/1974 |
| DE | 32 18 754 A1 | 11/1983 |
| DE | 32 48 768 A1 | 7/1984 |
| DE | 35 05 408 A1 | 2/1985 |
| DE | 34 11 892 A1 | 10/1985 |
| DE | 36 43 309 C1 | 3/1988 |
| DE | 38 18 213 A1 | 11/1989 |
| DE | 41 07 678 A1 | 9/1992 |
| DE | 100 15 005 A1 | 10/2001 |
| DE | 10 203 732 A1 | 8/2003 |
| DE | 10 2005 016 346 B3 | 1/2007 |
| DE | 10 2008 045 470 A1 | 3/2010 |
| EP | 0 098 930 A2 | 1/1984 |
| EP | 0282381 A1 | 9/1988 |
| EP | 0 578 152 A1 | 1/1994 |
| EP | 1 367 176 A1 | 12/2003 |
| EP | 2 161 375 A2 | 3/2010 |
| GB | 1 346 540 A | 2/1974 |
| GB | 2 133 155 A | 7/1984 |
| JP | 9-041863 A | 2/1997 |
| JP | 10-266783 A | 10/1998 |
| JP | 10-311717 A | 11/1998 |
| JP | 2009-167686 A | 7/2009 |
| WO | 03/087537 A1 | 10/2003 |

OTHER PUBLICATIONS

Supplementary European Search Report for European Application No. 13 86 2946 dated Jul. 20, 2016.

* cited by examiner

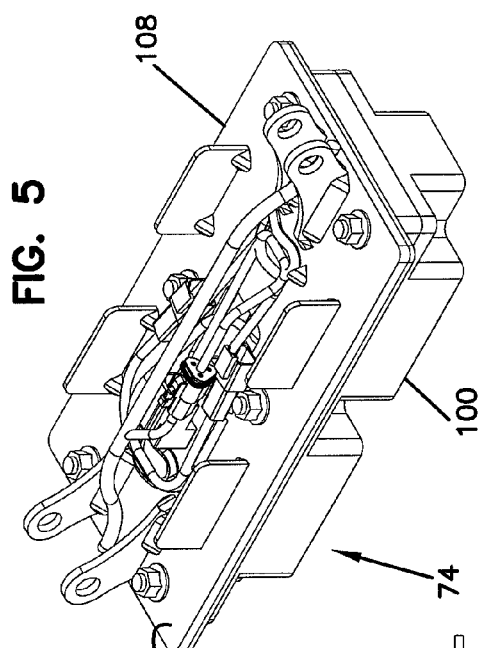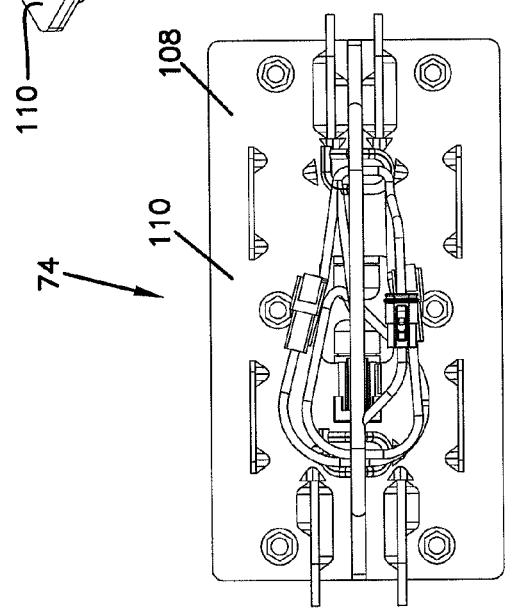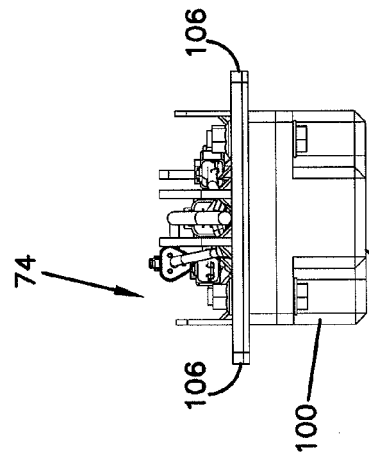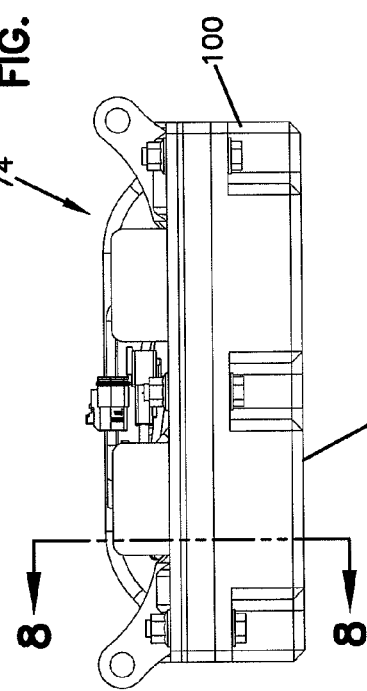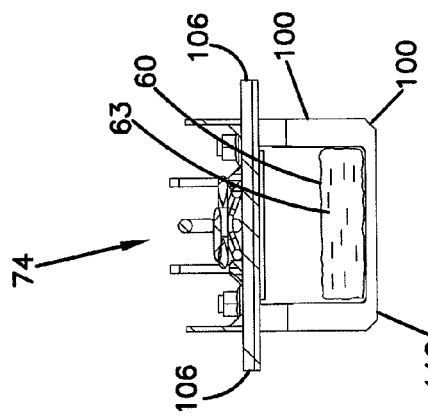

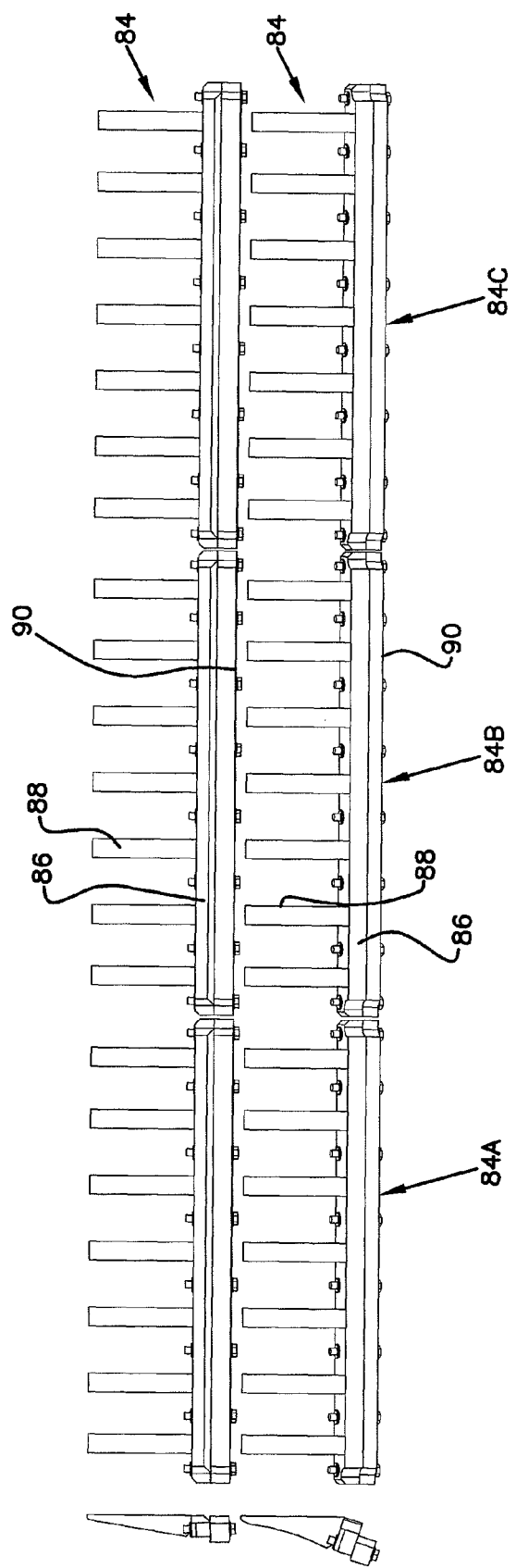

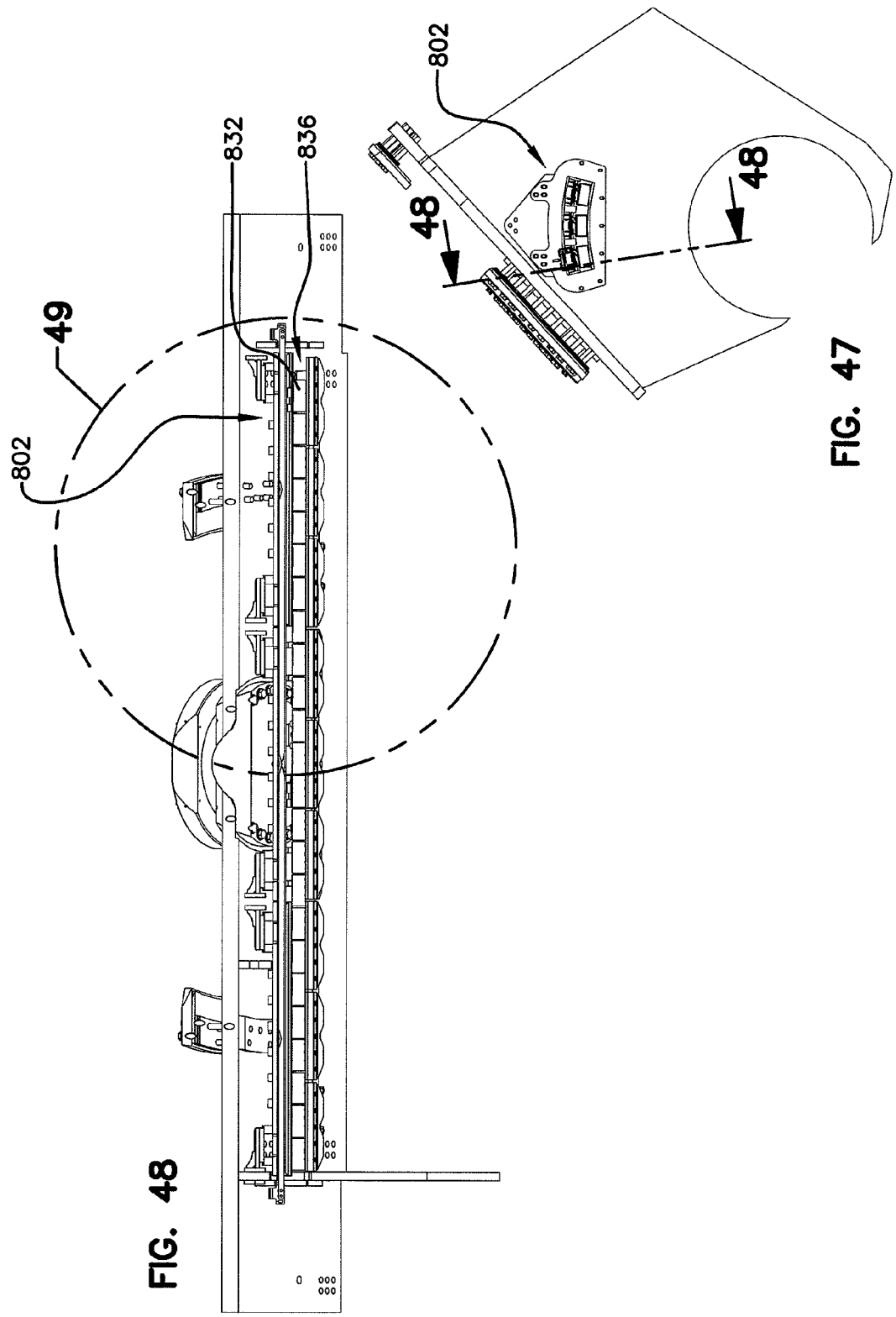

SYSTEMS AND METHODS FOR SENSING WEAR OF REDUCING ELEMENTS OF A MATERIAL REDUCING MACHINE

This application is a National Stage Patent Application of PCT/US2013/074672, filed Dec. 12, 2013, which claims benefit of U.S. Provisional Patent Application No. 61/736,303, filed Dec. 12, 2012, and which applications are incorporated herein by reference. To the extent appropriate, a claim of priority is made to each of the above disclosed applications.

TECHNICAL FIELD

The present disclosure relates generally to systems and methods for sensing wear in machines designed to reduce or break-down material. More particularly, the present disclosure relates to systems and methods for sensing wear of reducing elements used by excavation machines such as surface excavation machines.

BACKGROUND

Relatively hard materials are often processed for mining and construction. The variety of materials include rock, concrete, asphalt, coal and a variety of other types of earth formations. A number of different methods for reducing the size of these hard materials have been developed. One traditional material size reduction method has been to drill relatively small holes in the material which are then packed with an explosive that is ignited resulting in a rapid and cost effective method of size reduction. However, there are a variety of disadvantages to this technique including the inherent risk of injuries, the production of undesirable noise, vibrations, and dust, and the fact that this process is difficult to utilize in situations where space is limited or where there is a potential risk of causing other gases to ignite.

Due to the above-described disadvantages associated with blasting techniques, alternative methods have been developed for reducing relatively hard materials. The main alternative has been the use of reducing machines having rotary reducing components that move rigid and specialized reducing elements through paths of travel. The reducing components can include rotating drums that move the reducing elements through circular paths of travel. Such drums are typically attached to their corresponding machines so that the positions and orientations of the drum can be controlled to bring the reducing elements into contact with the material being reduced. Alternative reducing components can include boom-mounted chains that carry reducing elements. The chains are typically driven/rotated about their corresponding booms. The reducing elements are mounted to and move along the paths of travel defined by the chains. In use, the booms are moved (e. g., through a pivoting motion) to positions where the reducing elements are brought into contact with the material being reduced.

An example machine of the type described above is disclosed at U.S. Pat. No. 7,290,360. The disclosed machine is a surface excavation machine used for applications such as surface mining, demolishing roads, terrain leveling, and prepping sites for new construction or reconstruction by removing one or more layers of material. Surface excavation machines of this type provide an economical alternative to blasting and hammering and provide the advantage of generating a consistent output material after a single pass. This can reduce the need for primary crushers, large loaders, large haul trucks and the associated permits to transport materials to crushers.

The reducing elements of reducing machines have been developed to withstand the impact loads and abrasion associated with material reduction activities. Reducing elements can be constructed in a variety of shapes and sizes and have been labeled with various terms including cutters, chisels, picks, teeth etc. Typical reducing elements include leading impact points or edges and bases. The bases are constructed to fit into mounting structures that are integrated with drums or chains used to carry the reducing elements during material reducing applications. The harsh environment associated with material reducing applications virtually guarantees that the reducing elements will wear down over time. Thus the reducing elements are designed to be replaceable, while the mounting structures are not intended to be replaced frequently. For example, when a given reducing element becomes worn, it is removed from its corresponding mounting structure and replaced with a new, unworn reducing element.

Often, the tips or edges of the reducing elements have a harder construction (e.g., a solid carbide construction) than the bases of the reducing elements. When using new reducing elements to reduce material, the leading points or edges are exposed to the majority of the impacts and abrasion action. However, once the leading tips or edges becomes worn, the bases are exposed to more impacts and abrasive action. A variety of potential problems can arise when this occurs, including that the bases is less efficient at breaking the material causing inefficient operation. This inefficiency can result in generation of sparks and/or excessive heat which can lead to a risk of explosions, as may occur in a coal mining application where methane gas can be present. Additionally, the bases will typically wear relatively quickly as compared to the leading points or tips. This is significant because the bases prevent the reducing element mounting structures from being exposed to wear. Thus, once the leading edges or points of the reducing elements are worn away, the machines can only be operated for a relatively short period of time before the bases wear away resulting in a situation where the mounting structures of the drums or chains are contacting the material being reduced. Once a reducing elements are worn to this point, there is a risk of causing damage to the mounting structures of the drums or chains. The mountings structures are not intended to be repaired easily, so the resulting potential damage can be difficult and costly to repair.

As a result of these issues, there are significant benefits to replacing reducing elements before the wear has progressed to an unacceptable point. Systems have been designed to monitor the condition of cutters to allow operators to interrupt operation and replace cutters at appropriate times. Example systems for monitoring reducing element wear are disclosed in AT3826832; DE 10015005; and US 2010/0076697. While wear sensing systems exist, improvements are needed in this area.

SUMMARY

Aspects of the present disclosure relate to improved methods for sensing (e.g., detecting, measuring, monitoring, tracking, etc.) the wear state of a reducing element (i.e., a cutter, a pick, a chisel, a blade, a tooth, etc.) of a material reducing machine. In one example, the material reducing machine is an excavation machine such as a surface excavation machine used for mining, surface mining, terrain leveling, road milling, or other applications. In other examples, the material reducing machine can include a trencher, a rock wheel, a horizontal grinder, a tub grinder, a chipper or other type of machine that utilizes reducing elements to process a material by breaking up or otherwise reducing the size of the material.

A variety of additional aspects will be set forth in the description that follows. These aspects can relate to individual features and to combinations of features. It is to be understood that both the foregoing general description and the following detailed description are exemplary and explanatory only and are not restrictive of the broad concepts upon which the embodiments disclosed herein are based.

BRIEF DESCRIPTION OF THE DRAWINGS

FIG. 5 is a perspective view of an example sensing module for a reducing element wear sensing system in accordance with the principles of the present disclosure;

FIG. 6 is a plan view of the sensing module of FIG. 5;

FIG. 7 is a side view of the sensing module of FIG. 5;

FIG. 8 is a cross sectional view taken along Section 8-8 of FIG. 7;

FIG. 9 is an end view of the sensing module of FIG. 5;

FIG. 10 is a plan view of a breaker bar arrangement including two parallel breaker bar structures for use in protecting a sensor module array in accordance with the principles of the present disclosure;

FIG. 47 is a side perspective view of the multi-layer wear sensor protection system;

FIG. 48 is a cross-sectional view taken along section line 48-48 of FIG. 47.

DETAILED DESCRIPTION

Figure 1:
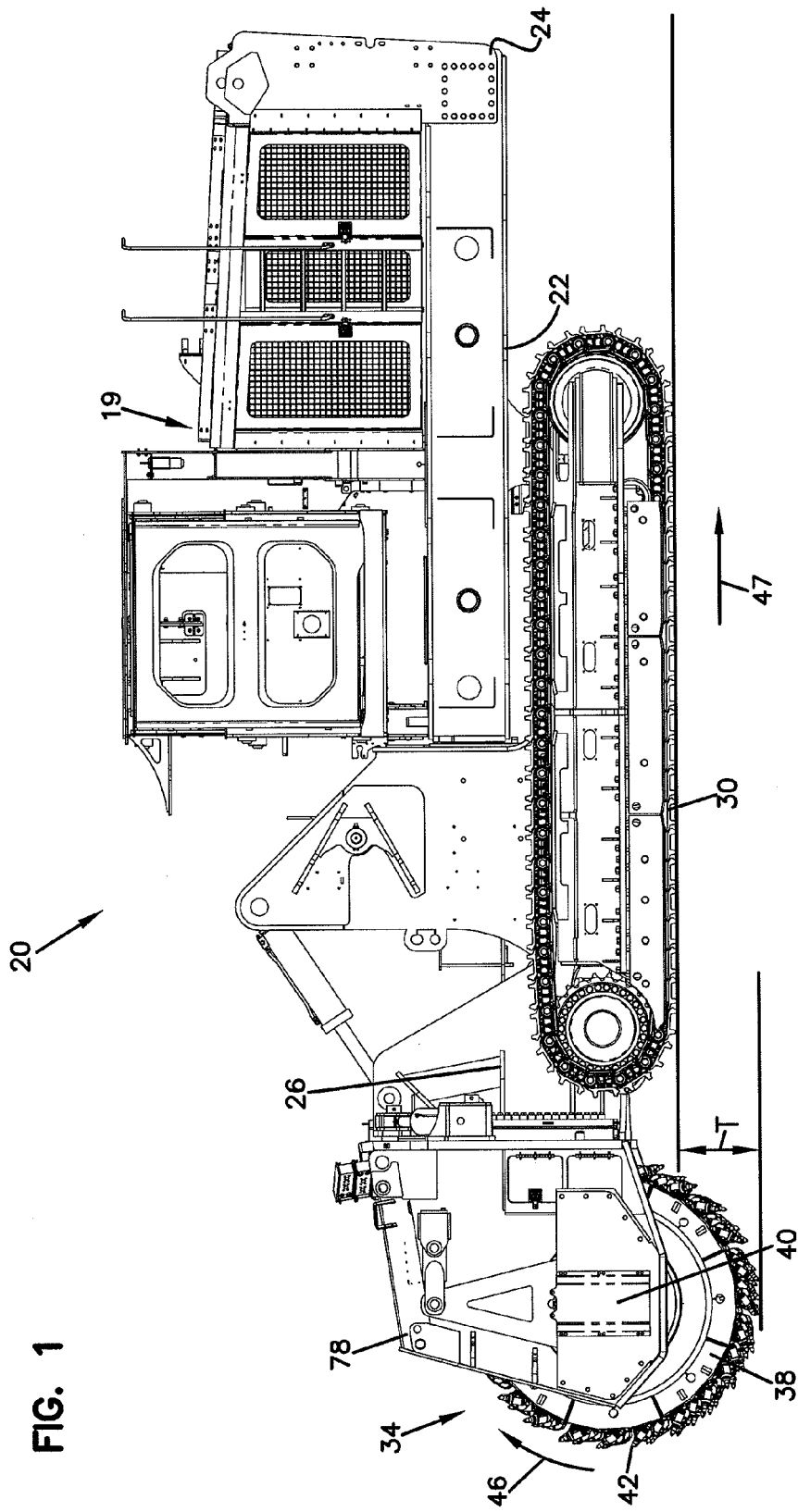
FIG. 1 is a side view of a surface excavation machine incorporating a reducing element wear sensing system in accordance the principles of the present disclosure.

The present disclosure relates generally to sensing systems for sensing reducing element wear in a material reducing machine. In one example, the material reducing machine includes a rotary component such as a drum or chain that carries the reducing elements. In certain examples, the reducing element wear sensing system provides an indication of the level of reducing element wear such that an operator can readily recognize when one or more of the reducing elements are in need of replacement. In certain examples, the level of reducing element wear can be displayed graphically or numerically to provide a qualitative indication of the specific level of wear for each reducing element. In other examples, the system can provide an indication when as worn beyond a predetermined level such that replacement is recommended.

Certain aspects of the present disclosure relate to reducing element wear sensing systems that use sensors to provide general data regarding the wear state of a given reducing element. For example, in certain examples, sensors in accordance with the principles of the present disclosure provide data regarding the general wear state of a given reducing element without determining or measuring the position of a specific geometric point or profile of the reducing element. The sensors can sense general physical characteristics (e.g., volume, mass, surface area, etc.) of the reducing elements without measuring the position of a given point on a given reducing element. Sensors of this type can be used effectively in harsh environments such as those encountered by material reducing machines (e.g., surface excavation machines, trenchers, rock wheels, horizontal grinders, tub grinders or other material reduction machines). In certain examples, sensing systems in accordance with the principles of the present disclosure can be used to assess reducing element wear of a reducing machine while the reducing machine is conducting reducing operations. Thus, sensing systems in accordance with the principles of the present disclosure can provide real-time wear information regarding the reducing elements of a reducing machine while the reducing machine is being operated. In certain examples, sensors of the sensing system are mounted in a sensing position and need not be moved from the sensing system to a stowed position when the reducing machine is used to reduce material. In certain examples, reducing element wear systems used in systems in accordance with the principles of the present disclosure can include inductive sensors.

Other aspects of the present disclosure relate to reducing element wear sensing systems that utilize various compensation, calibration or filtering techniques to process sensed data. In certain examples, sensing systems in accordance with the principles of the present disclosure can compensate for factors such as temperature and reducing element speed. In other systems in accordance with the principles of the present disclosure, sensors are placed in close proximity to one another and also in close proximity to multiple different reducing elements. For such applications, various strategies can be utilized to provide usable wear data regarding individual reducing elements. For example, filtering strategies can be utilized to filter out data corresponding to reducing elements not intended to be sensed by a given sensor. In certain examples, at least one sensor is provided for each reducing element. In certain examples, at least one sensor is provided for each reducing path defined by one or more reducing elements of a reducing machine. In certain examples, sensors are positioned in close proximity to one another and operating strategies are utilized to reduce or minimize interference between adjacent sensors. For example, sensors can be selectively activated and deactivated to minimize interference between adjacent sensors. The sensors can also be operated in sets so that multiple sensors can be activated at once without having adjacent sensors activated concurrently. In certain examples, a center to center spacing of the sensors is smaller than an effective sensing distance of the sensors. In certain examples, a spacing between reducing paths of the reducing elements of the material reducing machine is smaller than an effective sensing distance of the sensors used to sense wear of the reducing elements.

In certain examples, systems in accordance with the principles of the present disclosure can include structure for protecting the sensors of the sensing system during material reducing operations. For example, breaker bars or other blocking structures can be provided for preventing material from damaging the sensors. In certain examples, the breaker bars can be positioned closer to a reducing circle or cylinder of the material reducing machine than the sensors. In certain examples, the sensors can also be protected by a rugged, protective housing that covers the sensors but does not interfere with the sensors' ability to sense the reducing elements. In certain examples, the sensors can sense the reducing elements through the protective housings. In certain examples, protective housings are made of a dielectric material such as plastic and the sensors are inductive sensors.

In certain examples of the present disclosure, inductive wear sensors are used. In certain examples, the inductive wear sensors can have operating ranges of at least 75 mm when used with a standard target as defined by the sensor manufacturer. In certain examples, wear systems in accordance with the principles of the present disclosure can use inductive sensors having effective sensing distances less than 100 mm. In certain examples, the inductive sensors have effective operating distances greater than 50 mm.

Other aspects of the present disclosure relate to a wear sensing system including a multi-level wear sensor protection system. The multi-level wear sensor protection system includes a first level of protection, a second level of protection, and a third level of protection. In certain examples, the first level of protection includes an initial barrier layer including a plurality of sheet segments made of a polycarbonate material. The second level of protection includes a side-by-side arrangement of trays positioned behind the initial barrier layer. The trays can be configured to absorb impacts that are transmitted through the initial barrier layer to prevent the impacts from impacting upon the sensors. The third level of protection includes a relief structure for accommodating impacts that are transmitted through both the initial barrier layer and the trays. In one example, the relief structure can be positioned behind the trays for accommodating movement of the trays in response to an impact that passes through the initial barrier layer and the trays.

FIG. 1 illustrates a surface excavation machine 20 that can utilize a reducing element wear sensing system in accordance with the principles of the present disclosure. The surface excavation machine 20 includes a tractor 19 having a main chassis 22 (i.e., a mainframe) including a front end 24 and a rear end 26. The main chassis 22 is supported on a ground drive system (i.e., a propulsion system) that preferably includes a plurality of propulsion structures such as wheels or tracks 30 for propelling the machine 20 over the ground. An operator cab 32 is positioned at a top side of the main chassis 22. An excavation tool 34 is mounted at the rear end 26 of the main chassis 26. The excavation tool 34 includes an excavation drum 38 that is rotatably driven (e.g., by hydraulic motors) about a drum axis 40. The excavation drum 38 carries a plurality of reducing elements 42 suitable for cutting rock. The excavation drum 38 can be mounted to a boom that can be pivoted between a lowered excavating position (see FIG. 1) and a raised transport position (not shown). A shroud 78 at least partially surrounds/encloses the excavation drum 38.

Figure 2:
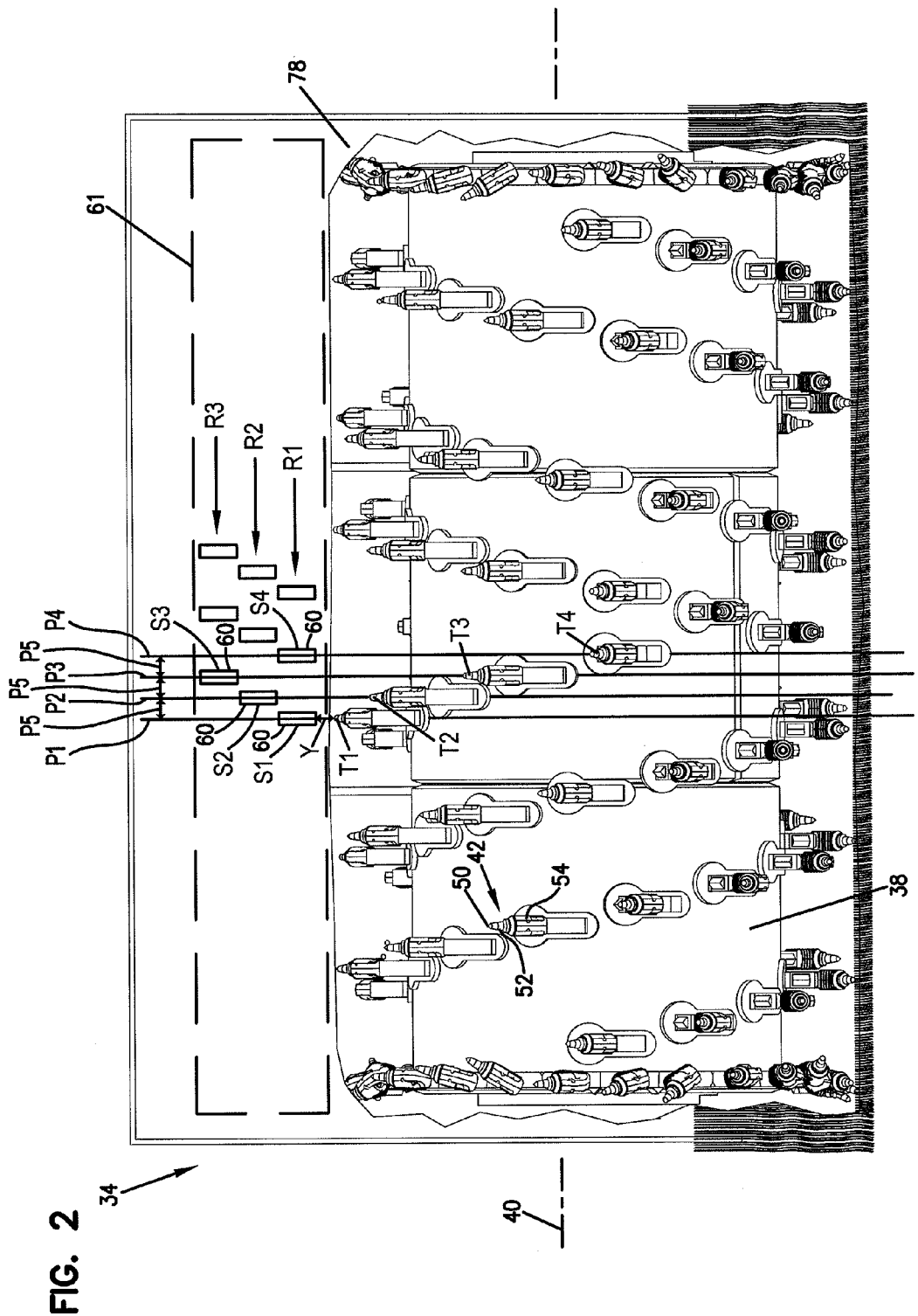
FIG. 2 is a rear view of the surface excavation machine of FIG. 1 showing an excavating drum and schematically showing a sensor array of the reducing element wear sensing system.

As shown at FIG. 2, the reducing elements 42 are depicted as teeth having leading tips 50 supported on bases 52. In certain examples, the leading tips 50 can be harder than the bases 52. For example, leading tips 50 can be solid, carbide inserts while the bases 52 can be hardened steel. In certain examples, the reducing elements 42 are removably mounted to the excavation drum 38. For example, the reducing elements 42 can be fastened within mounting structures such as pockets 54 integrated with the excavation drum 38.

In use of the surface excavation machine 20, the surface excavation machine 20 is moved to an excavation site while the excavation tool 34 is in the transport position. When it is desired to excavate at the excavation site, the excavation tool 34 is lowered from the transport position to the excavation position (see FIG. 1). While in the excavation position, the excavation drum 38 is rotated in a direction 46 about the axis 40 such that the excavation drum 38 uses a down-cut motion to remove a desired thickness T of material. As the excavation machine 20 moves in a forward direction 47, excavated material passes under the drum 38 and is left behind the surface excavation machine 20. During the excavation process, the tracks 30 propel the surface excavation machine 20 in the forward direction 47 thereby causing a top layer of material having a thickness T to be excavated. It will be appreciated that example excavation applications for which the surface excavation machine 20 can be used to include surface mining, road milling, terrain leveling, construction preparation and other activities. In other examples, the drum can be configured to excavate using an up-cut motion.

Figure 3:
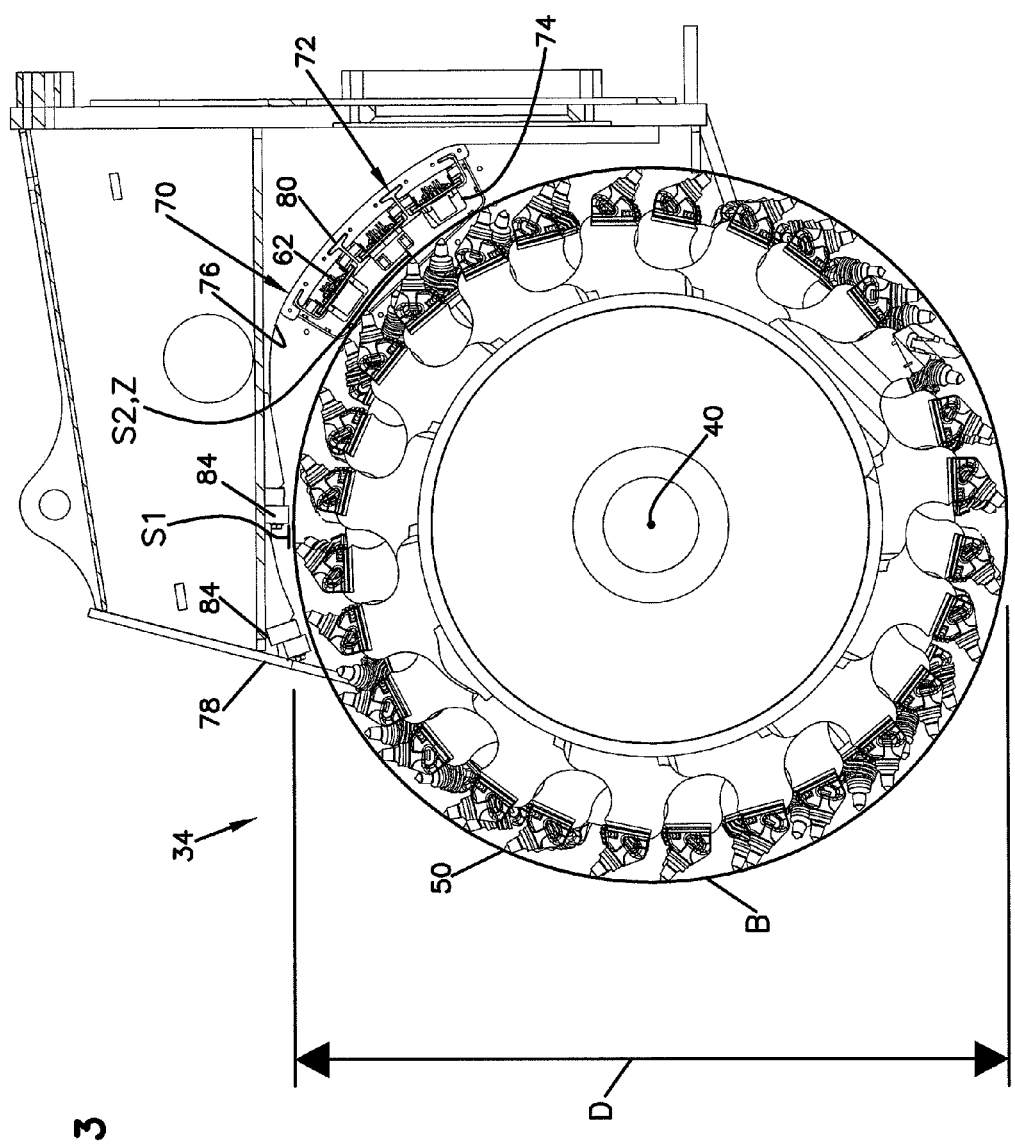
FIG. 3 is an end view of the excavating drum of FIG. 2 showing replaceable breaker bars and also showing the sensors of the reducing element wear sensing system.

Referring to FIG. 3, the leading tips 50 of the reducing elements 42 define a reducing boundary B (e.g., reducing circle or cylinder) of the excavation tool 34. The reducing boundary B corresponds to the generally cylindrical boundary transcribed by the leading tips 50 of the reducing elements 42 as the drum 38 is rotated about the drum axis 40. The reducing boundary B can have a reducing diameter D. The leading tips 50 of the reducing elements 42 also define reducing paths of the excavation tool 34. A reducing path is the path that the tip of a reducing element follows/defines when the drum is rotated. Each reducing path coincides with a reducing path plane that is perpendicular to the drum axis 40 and that passes through the leading tip 50 of the reducing element 42 that defines the reducing path. Example reducing path planes P1, P2, P3 and P4 for four different reducing paths are depicted at FIG. 2. The paths correspond to four different reducing elements 42. As shown at FIG. 2, a sensor array 61 can be provided within the shroud 78 near the reducing boundary B. In certain examples, a reducing path can be defined by a single reducing element 42 and a corresponding sensor of the sensor array 61 can be aligned with the reducing path so as to be capable of sensing the reducing element 42 when the reducing element 42 passes by the sensor as the reducing element 42 is rotated about the reducing boundary B by the drum 38. In certain examples, each reducing path of the excavation tool 34 can have a corresponding separate sensor. In other examples, two or more reducing elements 42 can be provided along a given reducing path.

Referring to FIG. 2, the reducing path planes P1, P2, P3 and P4 respectively coincide with reducing paths of reducing elements T1, T2, T3 and T4. The sensor array 61 can include separate sensors 60 corresponding to each of the reducing paths. The sensors 60 can have effective sensing distances Y that are longer than a path spacing PS between the reducing path planes. The sensors 60 can be arranged in multiple rows (e.g., three rows R1, R2 and R3) that extend along the axis of rotation 40 of the drum. The sensors 60 can be spaced a spacing distance Z from the reducing boundary B. The spacing distance Z is less than the effective sensing distance Y. The effective sensing distance Y can be larger than the path spacing PS defined between the reducing path planes. The sensors 60 of adjacent rows can be staggered relative to one another in an orientation that extends along the axis of rotation 40. In an example embodiment, adjacent reducing paths are not assigned to sensors in the same row. For example, as shown at FIG. 2, reducing path plane P1 aligns with sensor S1 of the first row R1, reducing path plane P2 aligns with sensor S2 of the second row R2, reducing path plane P3 aligns with sensor S3 of the third row R3 and sensor S4 aligns with sensor S4 of the first row R1. This pattern can repeat. In this way, the sensors 60 of the array can be arranged to have center-to-center sensor spacings measured along the axis of rotation 40 that match the path spacings PS. The effective sensing distances Y of the sensors 60 can be larger than the sensor spacings SS.

In certain examples, the reducing elements 42 each have a metal construction and the sensors 60 are inductive sensors. In use, the sensors 60 can generate alternating electromagnetic fields through which the reducing elements 42 pass as the reducing elements 42 are rotated about the axis of rotation 40 by the drum 38. Because the reducing elements 42 each have a metallic construction, when the reducing elements 42 pass through the electromagnetic fields of the sensors 60, eddy currents form on the surface of the reducing elements 42. The amount of energy that is transferred by this phenomenon is directly dependent upon the surface area of the reducing element 42 passing through the field. The amount of energy transferred from the magnetic field can be sensed by the inductive sensor and is represented by a decrease in electric current at the inductive sensor. Since the amount of energy transferred is dependent upon the size of the object passing through the magnetic field, the amount of current reduction sensed by the sensor as a reducing element passes through the magnetic field is representative of the size of the reducing element. As a reducing element wears during use, the surface area of the reducing element 42 passing through the magnetic field of its corresponding sensor is reduced such that less energy is transferred to the reducing element as the reducing element passes through the magnetic field. Since less energy is transferred to the reducing element, a smaller reduction in current is sensed by the inductive sensor. Thus, by monitoring the magnitude of current reduction sensed by the sensor as the reducing element passes through the magnetic field, it is possible to monitor the wear state of the reducing element corresponding to the sensor.

Figure 4:
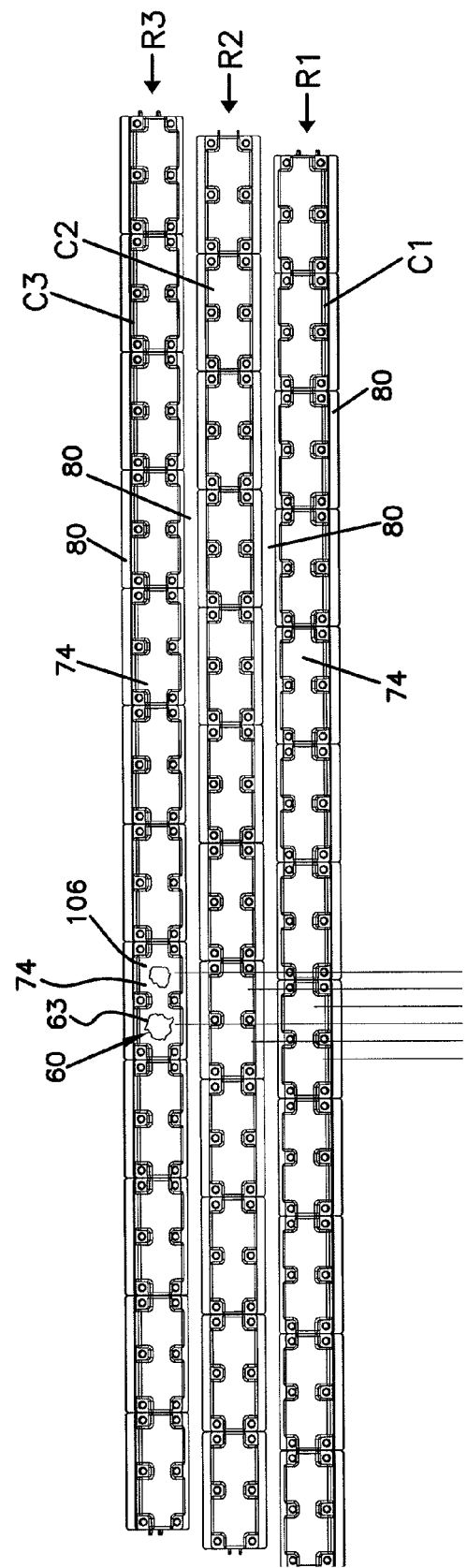
FIG. 4 is a sensor layout or array for the reducing element wear sensing system of FIG. 3.
Figure 11:
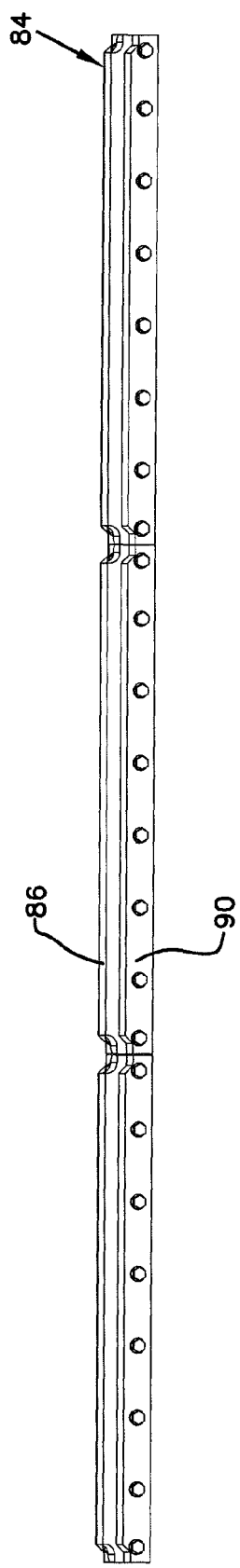
FIG. 11 is a profile view of one row of breaker bars of the breaker bar arrangement of FIG. 10.
Figure 12:
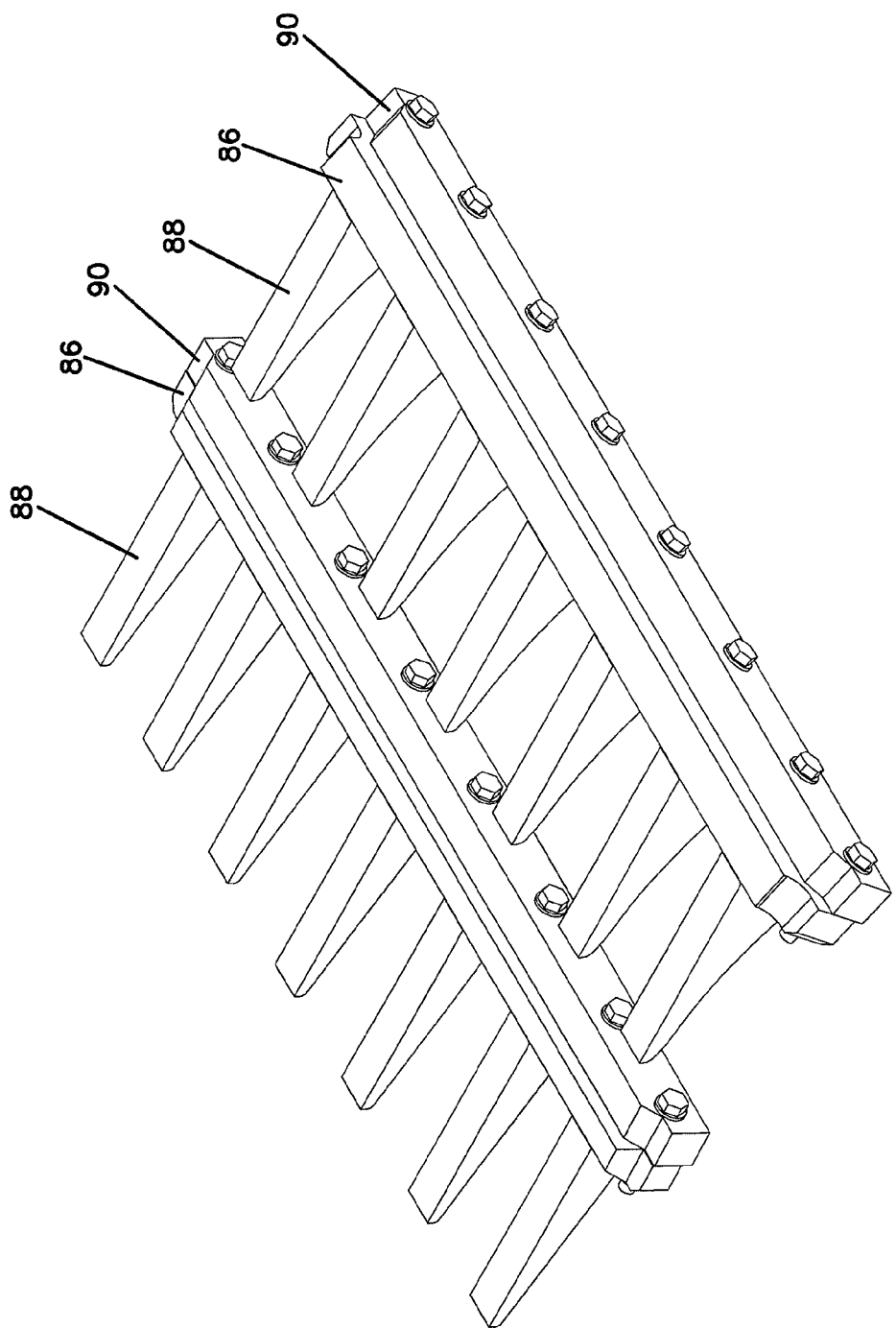
FIG. 12 is a perspective view showing first segments of each of the breaker bar structures of FIG. 10.

Referring to FIG. 3, the surface excavation machine 20 can include a wear sensing system 70 in accordance with the principles of the present disclosure. The wear sensing system 70 can include a hanger arrangement 72 for mounting sensor modules 74 to the surface excavation machine 20. In the depicted example, the sensor modules 74 are mounted at an interior surface 76 of the shroud 78 that at least partially surrounds the drum 38. The hanger arrangement 72 includes a plurality of rails 80 (e.g., tracks) having lengths that extend along the drum axis 40. The rails 80 define channels 82 in which a row of sensor modules 74 are received. As shown at FIG. 4, the sensor modules 74 can be arranged in an array having three parallel rows of R1, R2 and R3 of sensor modules 74. The rows R1, R2 and R3 correspond to channels C1, C2 and C3 defined by the rails 80 of the hanger arrangement 72. The sensor modules 74 can be coupled (e.g., pinned or otherwise fastened) together and can be loaded into the hanger arrangement 72 by sliding the rows of sensor modules 74 longitudinally into the channels C1, C2 and C3. It will be appreciated that openings can be provided in end walls of the shroud 78 for allowing the sensor modules 74 to be inserted into the channels C1, C2 and C3. During the insertion and removal process, the rows R1, R2 and R3 of sensor module 74 are slid along the channel C1, C2, C3 in an orientation that extends along the drum axis 40. When mounted in the channels, the sensor modules 74 of adjacent rows can be staggered relative to one another.

The wear sensing system 70 can also include blocking structure for preventing debris of substantial size from impacting the sensor modules 74. As shown at FIG. 3, material breaking structures are attached to the interior surface 76 of the shroud 78 at a location upstream from the sensor module 74. In certain examples, the material breaking structures are positioned at a spacing S1 from the reducing boundary B defined by the reducing elements 42 and the sensor modules 74 are positioned at a spacing S2 from the reducing boundary B defined by the reducing elements 42. In certain examples, the spacing S2 is larger than the spacing S1. In certain examples, the spacing S2 is at least 25%, 50% or 75% larger than the spacing S1. In certain examples, the spacing S2 is at least $\frac{1}{8}^{th}$ of an inch or at least $\frac{2}{8}^{th}$ of an inch or at least $\frac{3}{8}^{th}$ of an inch larger than the spacing S1. In certain examples, the spacing S2 is about $\frac{5}{8}^{th}$ of an inch and the spacing S1 is about one inch.

Referring still to FIG. 3, the breaking structure can include a plurality of breaker bar structures mounted to the interior side of the shroud 78. For example, FIG. 3 shows a breaker bar arrangement including first and second breaker bar structures 84. Each of the breaker bar structures 84 has a length that extends along the drum axis 40. The breaker bar structures 84 each include three breaker bar sections 84A, 84B and 84C that are aligned with one another to form the length of the breaker bar structure 84. Each of the breaker bar sections 84A, 84B and 84C includes a mounting bar 86 secured to the shroud 78 by reinforcing gussets 88. Each of the breaker bar sections 84A, 84B and 84C also includes an impact bar 90 fastened to the mounting bar 86. The impact bars 90 are positioned the spacing S1 from the reducing diameters D and are adapted to be impacted by material carried by the reducing elements 42 over the top side of the drum 38 during material reducing operations. As the material is impacted by the impact bars 90, the material is reduced in size such that the material is sufficiently small so as to not extend outwardly from the drum 38 a distance greater than the spacing S1. In this way, the material is prevented from significantly impacting the sensor modules 74. In certain examples, the impact bars 90 are secured to the mounting bars 86 by fasteners so that the impact bars can be readily removed and replaced as the impact bars 90 wear. As shown at FIG. 3, the two breaker bar structures 84 are spaced relative to one another about the circumference of the drum 38 such that one of the breaker bars structures 84 is positioned downstream of the other of the breaker bar structures 84. In this way, material is initially impacted by the upstream breaker bar 84 and then is subsequently impacted by the downstream breaker bar structure 84.

FIGS. 5-9 illustrate one of the sensor modules 74. The sensor module 74 is configured to hold two of the sensors 60. Each of the sensors 60 can include a separate magnetic coil 63 (see FIG. 4). The sensor module 74 includes structure for housing and protecting the magnetic coils. For example, the sensor module 74 includes a housing 100 including first and second chambers or sections 102, 104 for housing the coils 63 of the inductive sensors 60. The housing 100 is preferably made of a dielectric material through which magnetic fields generated by the coils 63 of the sensors 60 can be readily transmitted. In certain examples, housing 100 is made of a hard plastic material that provides impact protection to the sensors 60 while concurrently allowing magnetic fields generated by the sensors 60 to pass through the housing 100. As shown at FIG. 9, the housing 100 includes flanges 106 for engaging the rails 80 of the hanger arrangement 72 to retain the sensor modules 74 within the channels C1-C3. Electrical contacts and wiring can be provided on a back side 108 of the sensor module 74 for allowing the sensor module to be electrically connected to a control system having suitable control circuitry for controlling operation of the sensors 60. A metal backing plate 110 can be mounted at a back side of the housing 100. When the sensor module 74 is mounted within the hanger arrangement 72, a front face 112 of the housing 100 is positioned the spacing S2 from the reducing boundary B defined by the reducing elements 42. The sensors 60 are positioned slightly farther from the reducing boundary B than the front face 112. For example, the coils 63 of the sensor 60 can be positioned a distance from the reducing boundary B that is equal to the spacing S2 plus the thickness of the front wall of the housing 100. In certain examples, the front wall of the housing has a thickness of about ¼ of an inch and the sensors 60 are spaced about 1.25 inches from the reducing boundary B. It will be appreciated that in other examples, different spacings can be utilized depending upon the type of sensor used, the material being processed and the configuration of the reducing machine.

Figure 13:
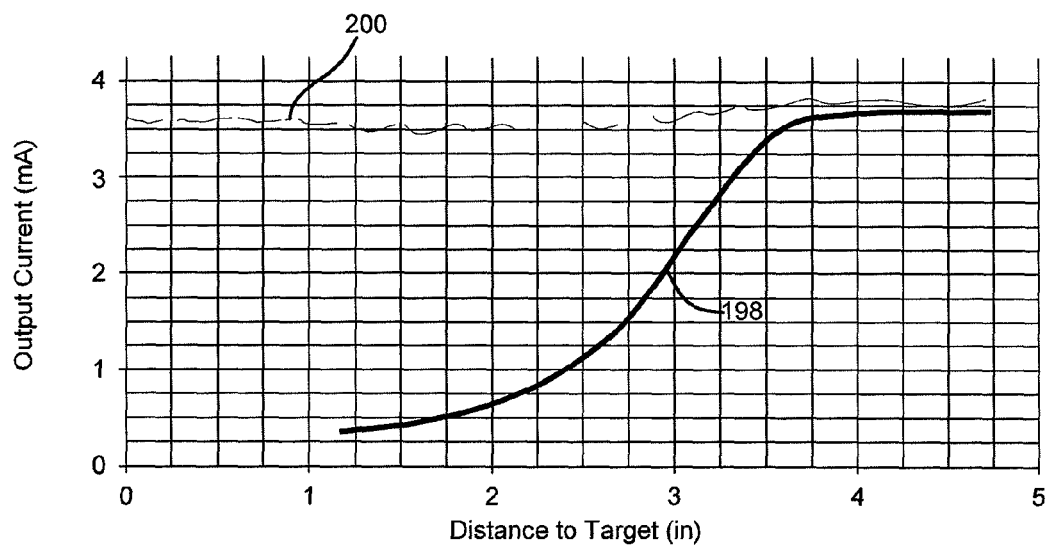
FIG. 13 is a graph showing inductive sensor outputs at different sensing distances for a standard target at room temperature.

It will be appreciated that the magnitude of the signal sensed by an inductive sensor is dependent upon the size of the target passing through the magnetic field of the sensor and/or the closeness of the target to the inductive sensor. FIG. 13 is a graph showing an output curve 198 of an inductive sensor at room temperature for a standard target. The output curve 198 of the graph of FIG. 13 shows the sensor output as a standard target is placed at different spacings directly in front of the sensor thereby causing the sensor to generate different outputs. When the standard target is outside the effective sensing range of the sensor, the inductive sensor output has a maximum value shown by line 200. As the standard target is moved progressively closer to the inductive sensor, the inductive sensor output gradually reduces in magnitude.

Figure 14:
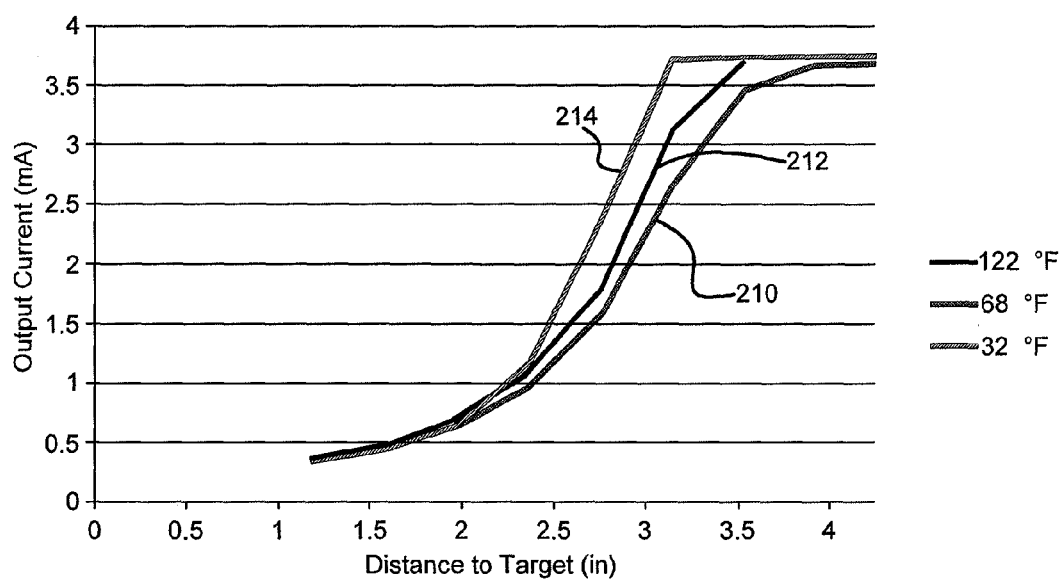
FIG. 14 is a graph showing inductive sensor outputs at different sensing distances for a standard target at different temperatures.

The impedance of the coil of the inductive sensor 60 changes with temperature. Thus, changes in temperature modify the output curve of the inductive sensor. For example, as shown at FIG. 14, the output curves of the inductive sensor move to the left and have steeper slopes as the temperature decreases. As shown at FIG. 14, line 210 corresponds to a temperature of 122° F., line 212 corresponds to a temperature of 68° F. and line 214 corresponds to a temperature of 32° F. The curves 210, 212 and 214 show outputs of a sensor when detecting a standard target at different distances for the different temperatures mentioned above.

The difference in inductive sensor output between a worn reducing element and a new reducing element can be small enough that temperature variations have a meaningful impact when assessing wear levels. Therefore, aspects of the present disclosure relate to using algorithms, look up tables or other means for compensating for temperature variations when monitoring reducing element wear. In certain examples, temperature sensors can be provided at the inductive sensor coils to provide an indication of the temperatures of the inductive sensor coils. In other examples, ambient temperature or another temperature associated with the reducing machine can be used to approximate the temperature of the coils of the inductive sensors.

Figure 15:
FIG. 15 is a graph showing sensor outputs at different sensing distances for a reducing element at room temperature with no lateral offset.

FIG. 15 shows an output curve 199 representing the output of an inductive sensor when sensing a reducing element at different distances from the inductive sensor. For the graph of FIG. 15, the reducing element is not offset from the inductive sensor (i.e., the coil of the inductive sensor and the reducing element are both aligned along a common plane corresponding to a reducing path of the reducing element). The reducing element used to provide the data of the graph of FIG. 15 has a smaller area than the standard target used to provide the data of FIG. 13. Thus, the sensor output curve 199 depicted at the graph of FIG. 15 has a steeper slope than the slope of the curve 198 depicted at FIG. 13.

Figure 16:
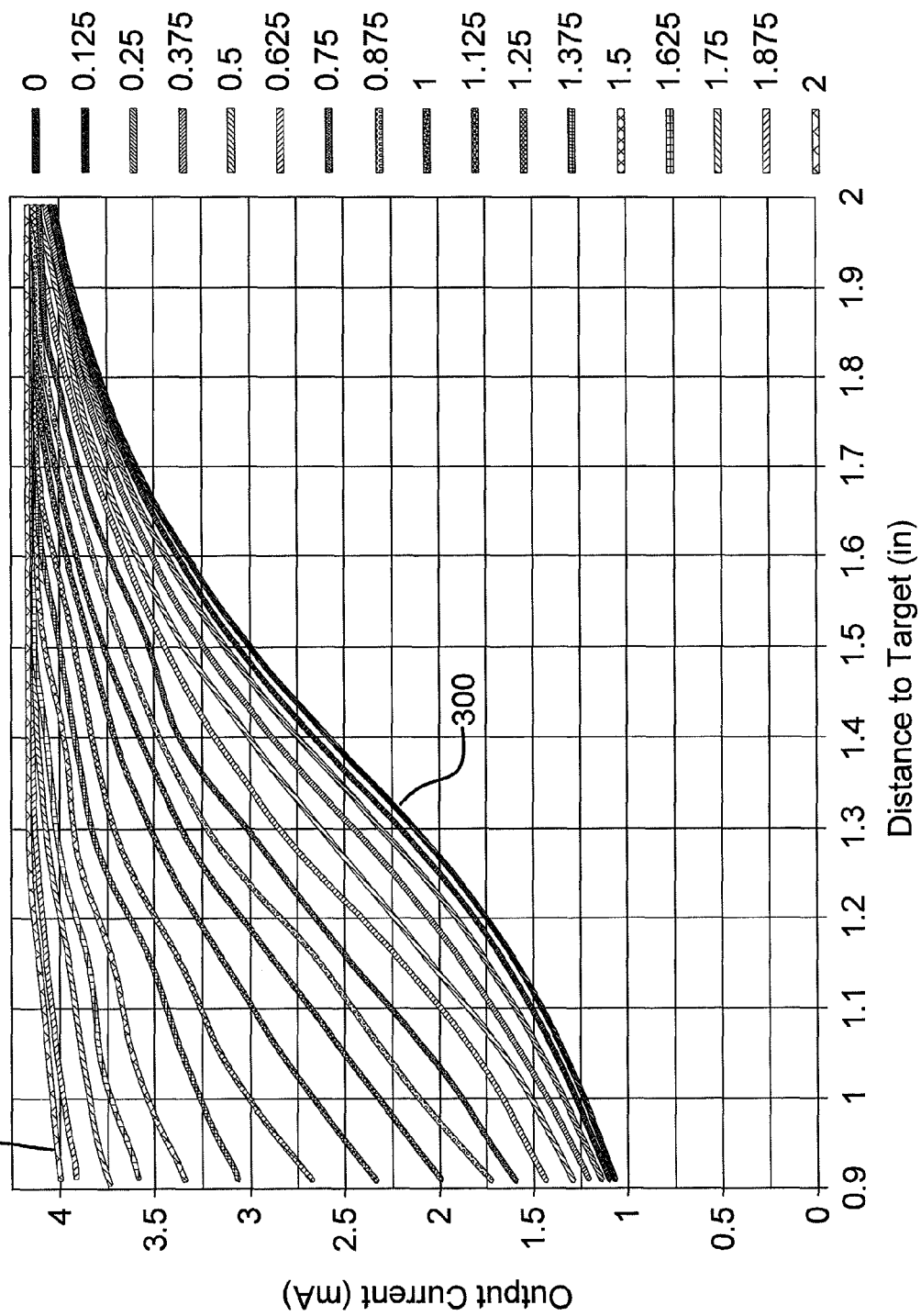
FIG. 16 is a graph showing sensor outputs at different sensing distances and various lateral offsets for a reducing tooth at room temperature.

In certain examples of the present disclosure, the coils of the inductive sensors can be placed at a center-to-center spacing measured along the axis of rotation 40 of the drum 38 that is smaller than the effective sensing distances of the inductive sensors and is also smaller than the widths of the magnetic fields generated by the inductive sensors. Thus, an inductive sensor aligned with a given reducing path can sense a reducing element corresponding to the reducing path, but also can sense reducing elements corresponding to adjacent reducing paths. As shown at FIG. 16, the slope of the output curve generated by the inductive sensor decreases as the lateral offset distance of the reducing element increases. For example, curve 300 shows the output response of an inductive sensor when a standard target is positioned at different distances from the inductive sensor while the standard target has zero lateral offset from the inductive sensor. In contrast, output curve 302 shows the output for the inductive sensor when the same target is positioned at the same outward distances as the output curve 300 but at a 2 inch lateral offset from the inductive sensor. The curves between the output curves 300, 302 show the effect of laterally offsetting the target from the inductive sensor.

Figure 18:
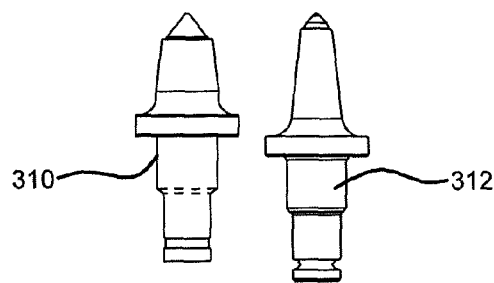
FIG. 18 illustrates the two teeth tested in the graph of FIG. 17.
Figure 17:
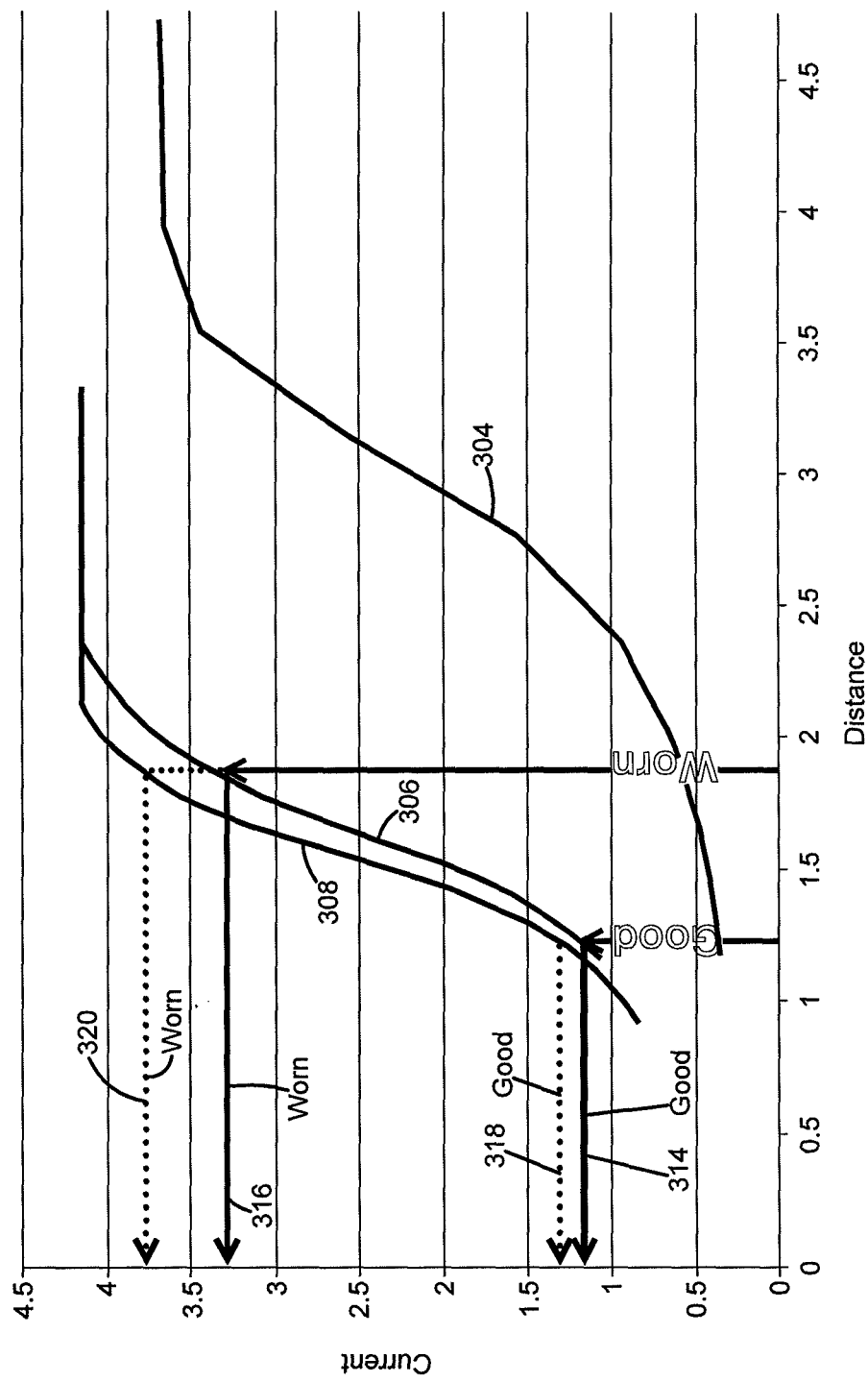
FIG. 17 is a graph comparing sensor outputs generated for a standard target and two different reducing element styles at various sensing distances and also illustrating a technique for identifying the wear status of a reducing element.

FIG. 17 shows three sensor output curves 304, 306 and 308. The sensor outputs for generating the curve 304 were generated by positioning a standard target at different distances from the inductive sensor while maintaining zero lateral offset. The inductive sensor outputs corresponding to the curve 306 were generated by positioning a reducing element 310 (see FIG. 18) at different distances from the inductive sensor while maintaining a lateral offset of zero. The inductive sensor outputs corresponding to the curve 308 were generated by positioning a reducing element 312 (FIG. 18) at different outward spacings from the inductive sensor while maintaining a lateral offset of zero. Since the reducing element 310 is thicker than the reducing element 312, the curve 306 has a less steep slope than the curve 308. FIG. 17 also illustrates a technique for assessing reducing element wear using the output from the inductive sensor. For example, with respect to the tooth 310, line 314 represents a baseline value for the tooth 310 when the tooth is new. This baseline value can be stored in memory of a control system (e.g., a computer, a processor, or other electronic device) and used to control operation of the wear sensing system. Line 316 is representative of an output of the inductive sensor when the tooth 310 becomes worn. In one example, the tooth 310 wears about ½ an inch between the line 314 and the line 316. In use, when the output value generated by the inductive sensor reaches the line 316, the operator can be notified that the corresponding tooth 310 should be replaced. Line 318 corresponds to an output from the inductive sensor when the reducing element 312 is new. Line 320 corresponds to an output from the inductive sensor when the reducing element 312 has worn to a state where the reducing element 312 should be replaced. Once again, a controller of the reducing element wear sensing system can monitor the outputs of the inductive sensor corresponding to the tooth 312 and can alert an operator that the tooth 312 should be replaced once the output of the inductive sensor reaches the line 320. As indicated above, the outputs of the inductive sensor can be modified by algorithms, look up tables or other means to compensate for factors such as temperature and speed. In this regard, it is noted that the speed at which the reducing element is traveling when the reducing element passes through the alternating magnetic field of the inductive sensor can also affect the output of the sensor. For example, as the rotational speed of the drum is increased without changes an outward spacing between the inductive sensor and the reducing element being sensed, the change in current sensed by the sensor as the reducing element passes through the magnetic field is reduced. To overcome this factor, an algorithm can be used to modify the output of the inductive sensor to compensate for the rotational speed of the drum.

Figure 19:
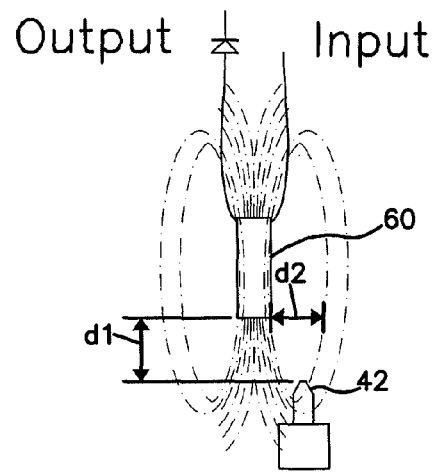
FIG. 19 illustrates a reducing element that is laterally offset from a sensor.
Figure 20:
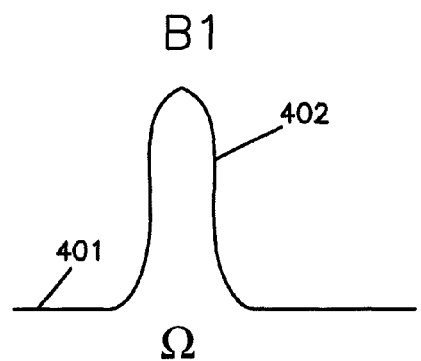
FIG. 20 illustrates an output of the sensor with the reducing element laterally offset as shown in FIG. 19.
Figure 21:
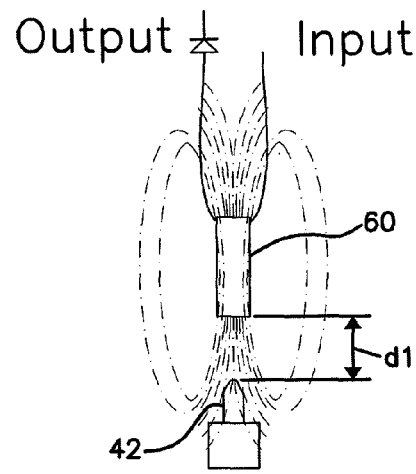
FIG. 21 shows a reducing element aligned with a sensor.
Figure 22:
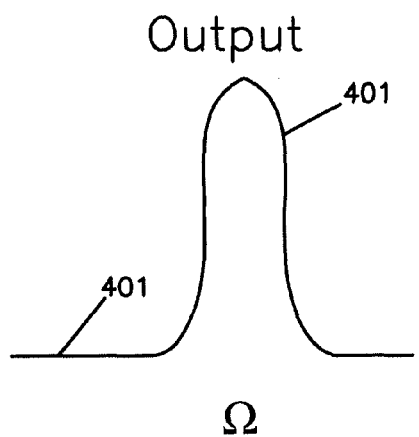
FIG. 22 shows an output from the sensor with the reducing element aligned as shown at FIG. 21.

FIG. 21 shows a reducing element 42 interfering with the magnetic field of a sensor 60 and therefore being detected by the sensor 60. The reducing element 42 is shown at an outward spacing distance d1 and a lateral spacing distance of zero. FIG. 22 shows an output of the inductive sensor with the reducing element at the position of FIG. 21. FIG. 19 shows the reducing element 42 laterally offset from the sensor 60 by a lateral spacing distance d2. The reducing element 42 is also offset from the inductive sensor 60 by the outward spacing distance d2. The outward spacing distance d1 is the same at FIGS. 19 and 21. FIG. 20 shows an output of the inductive sensor 60 with the reducing element 42 in the position of FIG. 19. A comparison of FIGS. 20 and 22 shows that an output signal 401 generated by the sensor 60 when the reducing element 42 is directly in line with the inductive sensor 60 has a larger variance as compared to a non-sensing reading 401 of the sensor 60 than a corresponding output signal 402 generated by the inductive sensor 60 when the reducing element 400 is positioned at the same outward spacing distance d1 but also at a lateral spacing distance d2. The graph of FIG. 20 also demonstrates that inductive sensors 60 are capable of sensing reducing elements that are laterally offset from the sensors but still within the magnetic field of the sensor.

Figure 23:
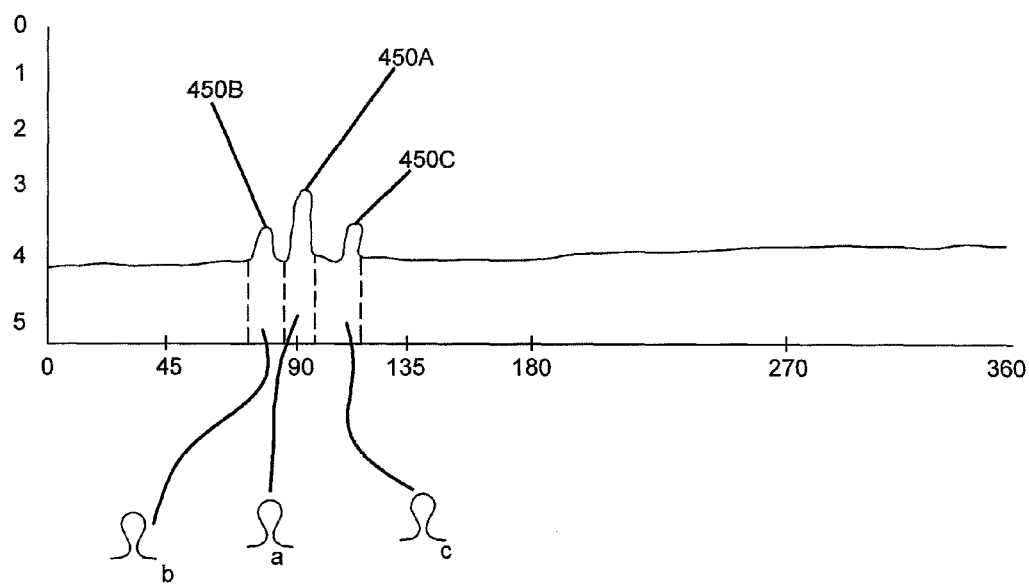
FIG. 23 illustrates a sensor output profile prior to filtering where the profile includes a major output corresponding to a reducing element aligned with the sensor and minor outputs corresponding to reducing elements offset from the sensor.
Figure 24:
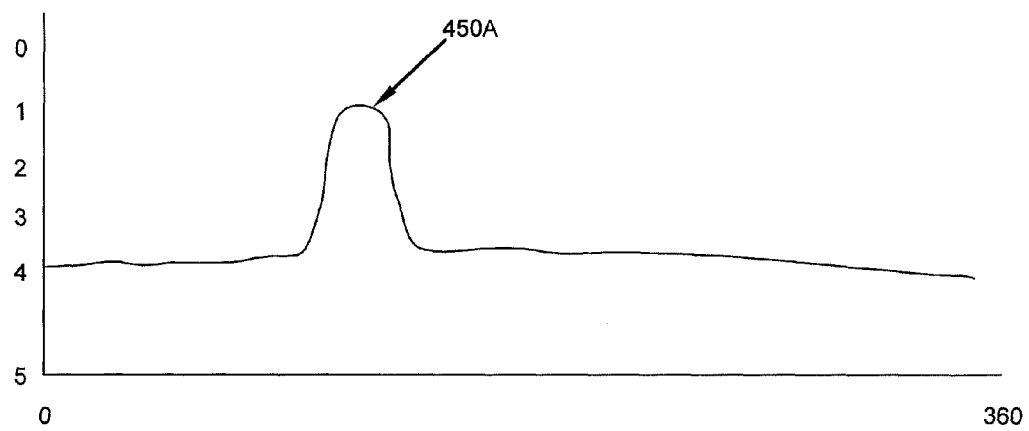
FIG. 24 is a graph illustrating the profile of FIG. 23 with the minor outputs filtered out.

As shown at FIGS. 19 and 20, reducing elements that are laterally offset from a given inductive sensor 60 can be detected by the inductive sensor 60 as the reducing elements move past the sensor 60. In certain examples of the present disclosure, the cutting paths defined by the reducing elements 42 can be sufficiently close together that one of the inductive sensors 60 can detect the reducing elements corresponding to three or more of the reducing paths. For example, FIG. 23 shows an initial, unfiltered sensor output profile for the inductive sensor 60 for one rotation of the drum 38. As the drum 38 rotates, the inductive sensor 60 senses the reducing element 42 that is aligned with the inductive sensor 60. The sensor 60 also senses the reducing element 42 corresponding to the reducing path that is offset to the left of the inductive sensor 60 and the reducing element 42 that corresponds to the reducing path offset to the right of the sensor 60. Because the left and right reducing elements are laterally offset from the sensor 60, signal readings 450B and 450C corresponding to such reducing elements have a smaller variance in magnitude as compared to a reading 450A corresponding to the aligned reducing element. As indicated at FIG. 23, rotational positions $\Omega_a$, $\Omega_b$ and $\Omega_c$ of the center, left and right reducing elements are determined and saved in memory. During a filtering process, the magnitudes of the readings 450A, 450B and 450C are compared and the reading 450A with the greatest variance from zero is selected. The rotational position $\Omega_a$ of the highest reading 450A is saved in memory. The readings 450B and 450C can then be filtered out as shown at FIG. 24. Thereafter, the control system will only look for inductive sensor reading values corresponding to the aligned reducing element at the rotational position $\Omega_a$. If the system does not detect a reducing element at the rotational position $\Omega_a$, then the operator can be notified that the aligned reducing element is missing. As the reducing element wears, the magnitude of the signal reading 450A at rotational position $\Omega_a$ will change. A certain magnitude of change of the signal reading 450A as compared to a base-line signal reading value (e.g., the reading when the reducing element was new) is indicative of the reducing element being worn to a point where the reducing element 42A should be replaced. At this point, the operator can be notified that the reducing element 42A should be changed.

In certain examples, the inductive sensors 60 are positioned sufficiently close to one another that the magnetic fields of adjacent sensors 60 overlap one another. Thus, if all the sensors 60 were operated simultaneously, the magnetic fields of adjacent sensors could interfere with one another. To prevent this type of magnetic interference, in certain examples, all of the sensors 60 are not operated at the same time. For example, in one example, each of the sensors 60 can be individually operated such that readings are individually taken with respect to each of the reducing paths. In such an example, the controller can use a control protocol that repeatedly cycles through the sensors with each sensor being individually actuated for at least one rotation of the drum 38. In other embodiments, steps or groups of the sensors 60 can be simultaneously actuated and the control system can cycle through the groups of sensors 60. In certain examples, the sensors of each group can be selected based on the relative positioning of the sensors and the positioning of their corresponding magnetic fields. Specifically, the sensors of any given set are selected so that the magnetic fields of the sensors within the set do not interfere with one another.

Figure 25:
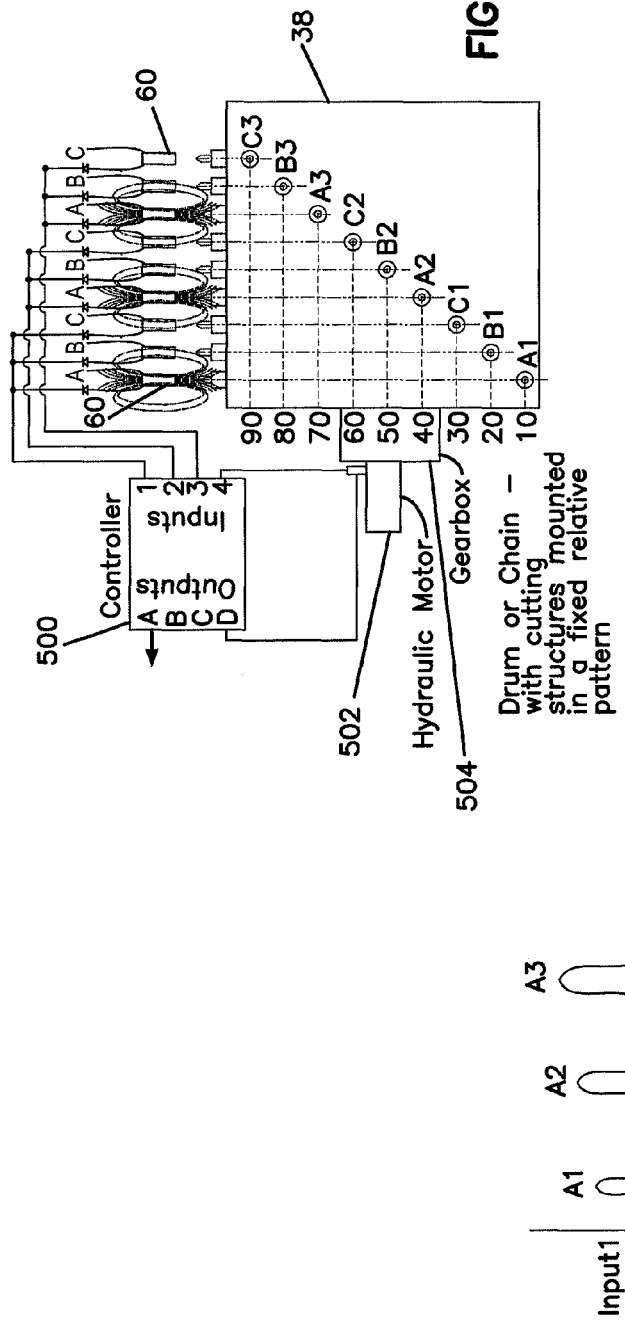
FIG. 25 shows a portion of an excavating drum having first, second and third sets of reducing elements and also illustrates a portion of a sensing system including first, second and third sets of sensors corresponding to the first, second and third sets of reducing elements, in FIG. 25 the first set of sensors is activated so as to sense the wear state of the first set of reducing elements and the second and third sets of sensors are deactivated.
Figure 26:
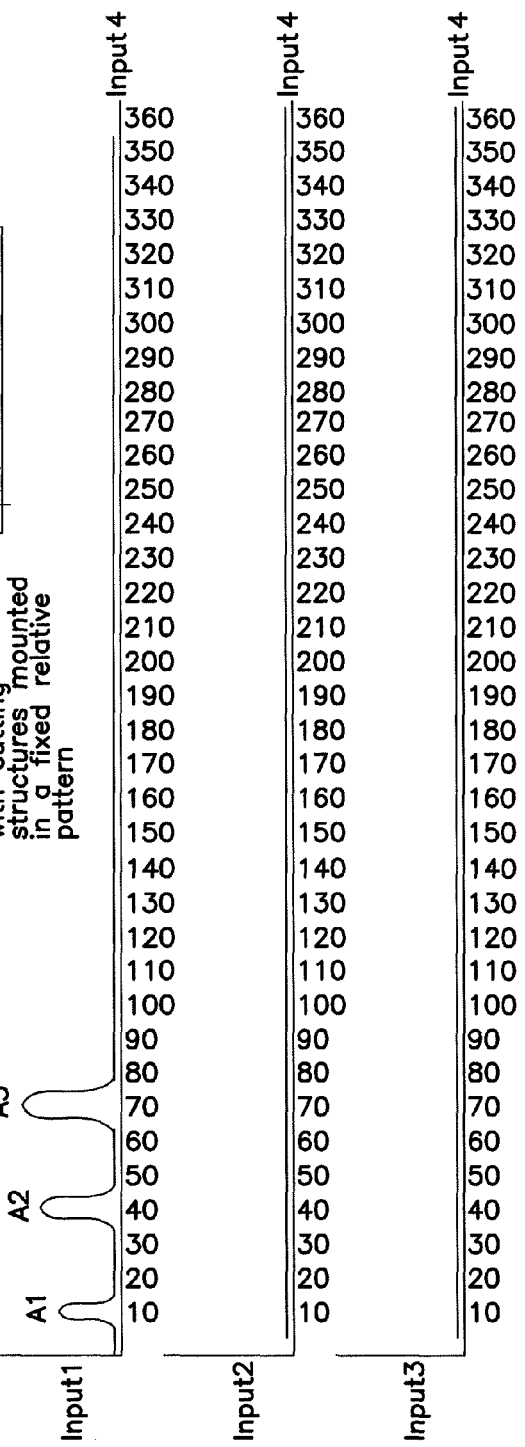
FIG. 26 shows the wear state profiles of the first, second and third sets of sensors of FIG. 25 with only the first set of sensors activated as shown at FIG. 25.
Figure 27:
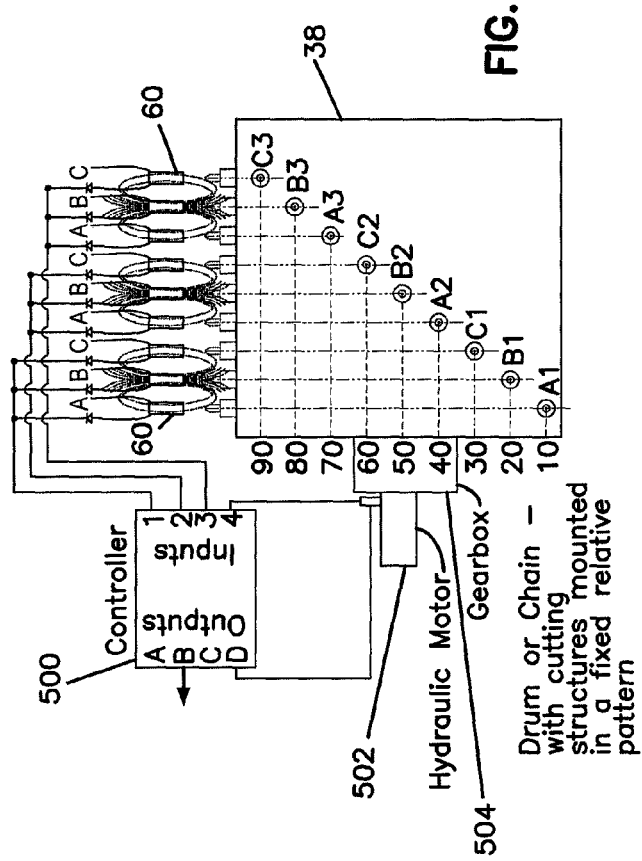
FIG. 27 shows the arrangement of FIG. 25 with the second set of sensors activated and the first and third sets of sensors deactivated.
Figure 28:
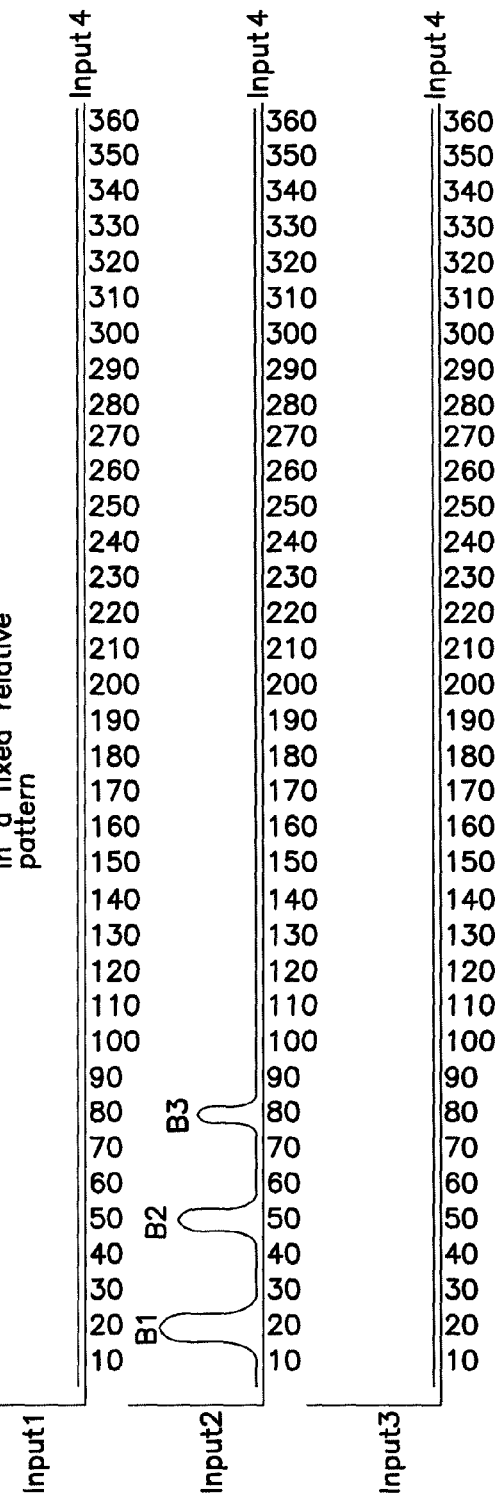
FIG. 28 shows the wear profiles for the first, second and third sets of sensors with only the second set of sensors activated as shown at FIG. 27.
Figure 29:
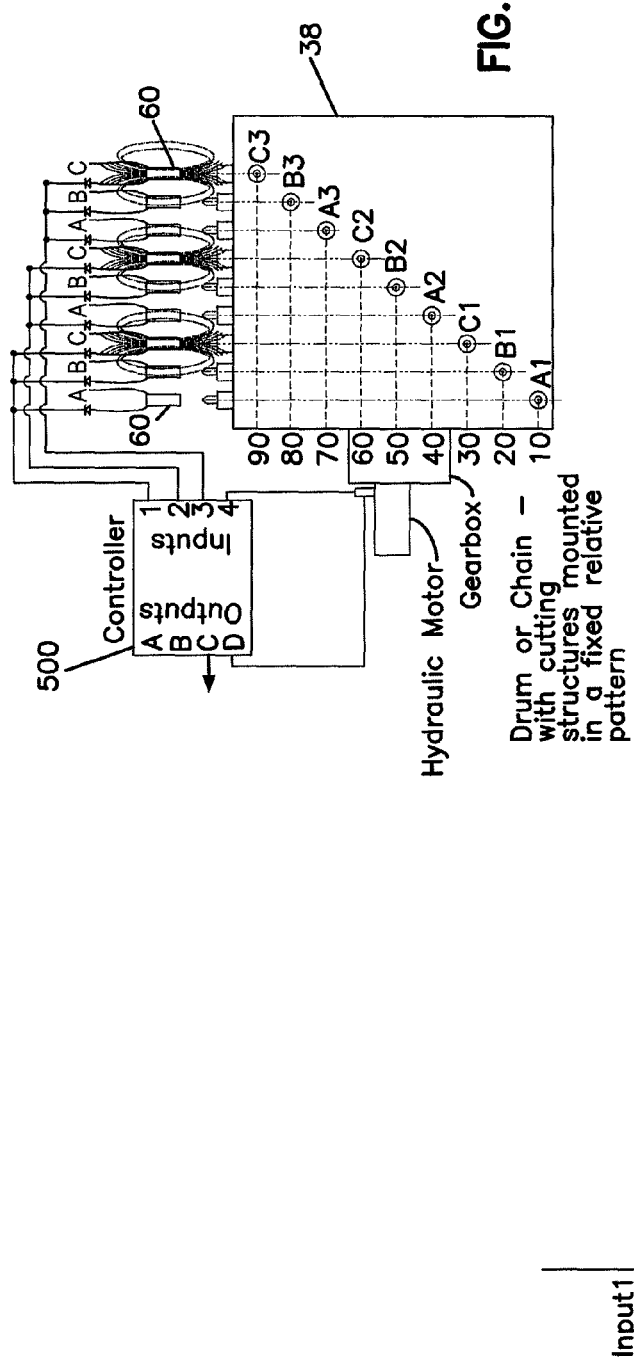
FIG. 29 shows the arrangement of FIG. 25 with the third set of sensors activated and the first and second sets of sensors deactivated.
Figure 30:
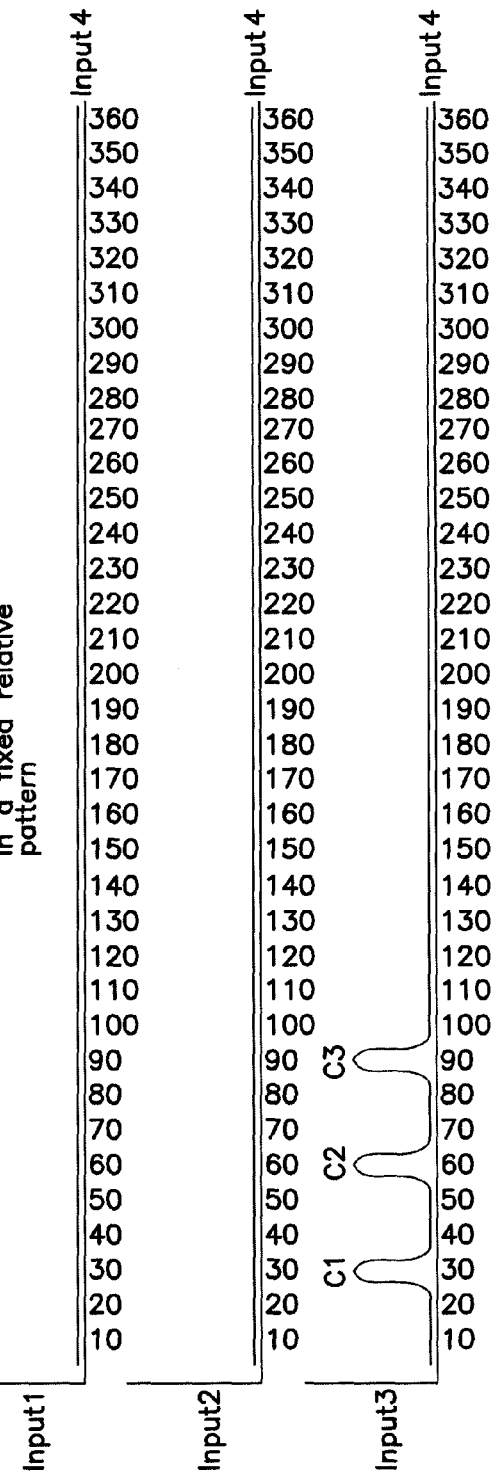
FIG. 30 shows reducing element wear profiles for the first, second and third sets of sensors with only the third set of sensors activated as shown at FIG. 29.

FIGS. 25-30 relate to a system having multiple sets of sensors 60 that are sequentially energized in de-energized. As shown at FIGS. 25, 27, and 29, only a portion of the length and the circumference of the drum 38 are depicted in a laid-flat view. For example, only about 90° of the circumference of the drum is depicted and only ¼ of the length of the drum is depicted. The depicted portion of the drum includes reducing elements A1, B1, C1, A2, B2, C2, A3, B3, and C3. The sensing system includes a first set of sensors A, a second set of sensors B and a third set of sensors C that all interface with a controller 500. The controller 500 controls the operational speed of the drum 38 via a hydraulic motor 502 and a gear box 504. The controller also controls operation of the inductive sensor sets A, B and C. For example, during a first sensing phase, the inductive sensors corresponding to set A are activated and the inductive sensors corresponding to sets B and C are deactivated. With the sensors of set A activated and the sensors of sets B and C deactivated, near readings are taken for the reducing elements A1, A2 and A3 as shown at FIG. 26 and no readings are taken for the reducing elements corresponding to sets B and C. As shown at FIG. 26, specific reading values (e.g., input 1 from inductive sensors) and rotational positions (input 4) for each of the reducing elements A1, A2 and A3 are identified by the controller. During the first phase of sensing, the sensors of set A sense the wear level of the reducing elements A1, A2 and A3 as the drum rotates through one or more rotations.

After the first phase of sensing, the controller implements a second phase of sensing in which sensor sets A and C are de-energized, and sensor set B is energized (FIG. 27). The controller takes wear readings (e.g., input 2 from the inductive sensors of set B) for reducing elements B1, B2 and B3 as shown at FIG. 28. The input 2 values correspond to the wear levels of reducing elements B1, B2 and B3. The controller can have pre-saved information relating to the rotational positions of the reducing elements B1, B2 and B3. Additionally, the controller can compare sensed wear level values generated by the sensor set B corresponding to each of the reducing elements B1, B2 and B3 and can compare such values to base level wear values of the reducing elements B1, B2 and B3. The base level wear values can correspond to values established when the reducing elements B1, B2 and B3 were initially installed on the drum 38. In comparing the sensed wear level values generated by the sensor set B for each of the reducing elements B1, B2 and B3 to their corresponding baseline wear levels, the controller can use algorithms or other means to compensate for variations associated with temperature, the rotational speed of the drum or other factors. Once wear readings for the reducing elements for B1, B2 and B3 have been established, the controller can stop the second phase of sensing and move to a third phase of sensing.

FIG. 29 shows the system in a third phase of sensing. In the third phase of sensing, the sensor sets A and B are de-energized, and the sensor set C is energized. With the sensor set C energized, the controller can access input 3 values from the sensors of set C relating to the wear levels of the reducing elements C1, C2 and C3 (see FIG. 30). Typically, the wear level values are generated by the sensor set C as the drum is rotated. The sensed wear level values of the reducing elements C1, C2 and C3 can be compared to base-line wear level values for the reducing elements C1, C2 and C3. The base-line wear level values for the reducing elements C1, C2 and C3 can be established by the system when the reducing elements C1, C2 and C3 are initially installed on the drum 38. If the sensed wear level values indicated by input 3 deviate from the base-line wear level values by a predetermined amount, the system can indicate that replacement of one or more of the reducing elements C1, C2 and C3 is recommended or required.

It will be appreciated that certain readings taken by inductive sensors in accordance with the principles of the present disclosure are general in nature and do not identify the position of a specific geometric point on any of the reducing elements. Instead, the readings taken by the sensors provide a general indication of the overall surface area of a given reducing element that passes through the magnetic field of the sensor corresponding to the reducing element. The reading can vary depending upon the size and shape of the reducing element. In this regard, different wear patterns on the reducing element can yield similar readings. For example, similar yield readings may be yielded if portions of the base wear away while the tip remains intact or if the tip is removed and the base remains fully intact. Advantageously, sensing systems in accordance with the principles of the present disclosure provide a good indication of general wear while concurrently not using precise optical technology that is not compatible with use during normal operation of the reducing machine. Thus, sensing systems in accordance with the principles of the present disclosure can be used while their corresponding material reducing machines are being used to reduce materials and do not require material reduction operations to be stopped to allow for wear sensing. Additionally, sensing configurations in accordance with the principles of the present disclosure have rugged constructions that can remain in a sensing position during material reduction operations and are not required to be moved to a stowed position during material reduction operations.

In practice of aspects of the present disclosure, a reducing element is initially installed on a drum or chain. The drum and/or chain is then rotated and a base-line wear reading is taken with respect to the installed reducing element. The base-line wear reading can be taken using a sensor such as an inductive sensor. At the time the base-line wear reading is taken, a temperature value (e.g., a temperature representative of the coil temperature) and a rotational speed of the drum or chain are identified. The base-line wear reading as well as the temperature value and the rotational speed value can be saved in memory. The machine can then be operated to perform material reduction operations. While performing material reduction operations, a real-time wear reading can be taken with respect to the reducing element using the sensor. Real-time temperature and rotational speed readings can also be taken. Once the real-time readings have been taken, the real-time wear reading and the base-line wear reading can be compared to assess a wear level of the reducing element and to determine whether the reducing element has worn to the point where the reducing element is recommended or required to be replaced. In comparing the real-time wear reading to the base-line wear reading, the controller can make adjustments to the real-time wear level value and/or the base-line wear level value to compensate for any differences that may exist between the base-line temperature value and the real-time temperature value and/ or between the base-line rotational speed and the real-time rotation speed. If the base-line and real-time wear readings differ by a predetermined amount after compensation, the controller can provide an indication to an operator that replacement of the reducing element is recommended or required.

At initial installation of the reducing element, the controller can determine a rotational position of the reducing element and filter out readings corresponding to reducing elements not desired to be sensed for the particular sensing operation being performed. When the controller takes the real-time wear reading, the controller looks for a reading from the sensor at the pre-identified rotational position of the chain or drum that corresponds to the reducing element in question. If no reading is detected at the pre-identified rotational position, the controller recognizes that the reducing element is missing and provides an indication to the operator that the reducing element is missing and repair or replacement is needed.

Figure 31:
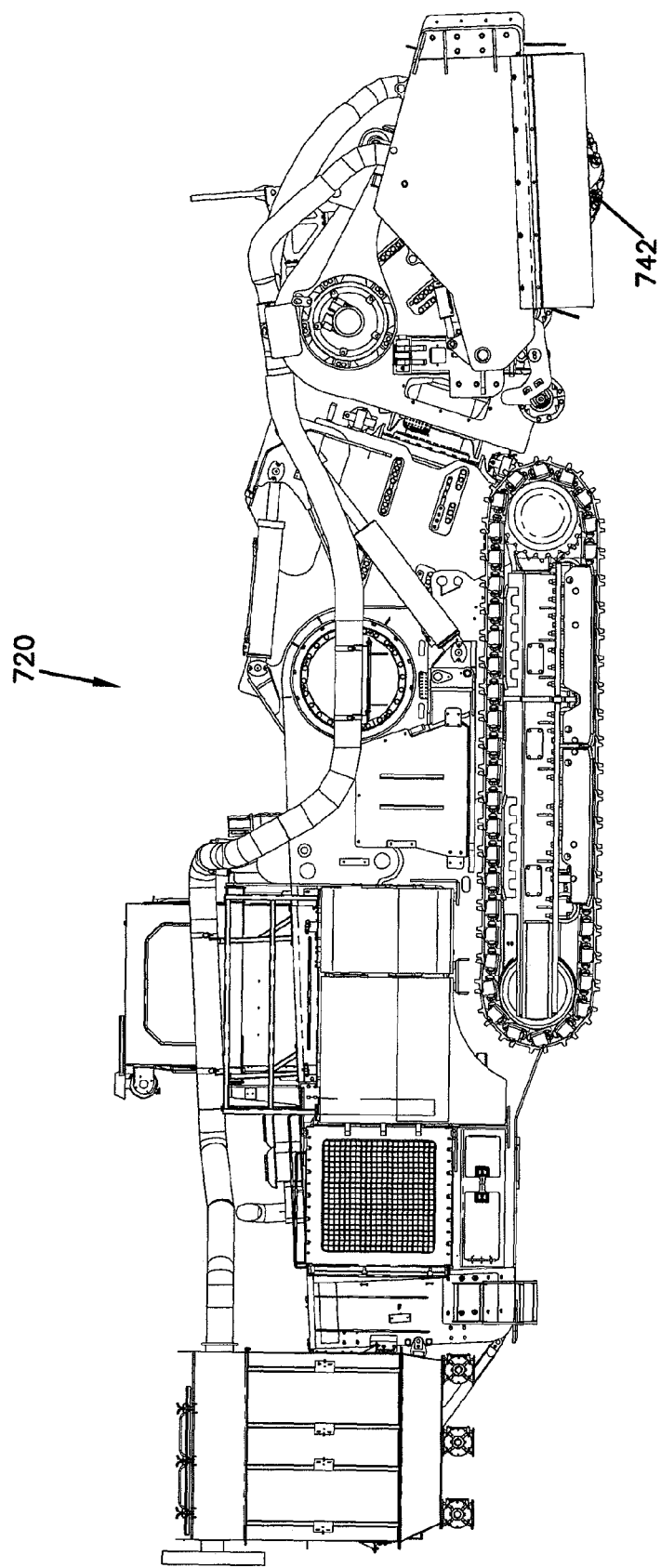
FIG. 31 is a side view of another surface excavation machine suitable for utilizing a reducing element wear sensing system in accordance with the principles of the present disclosure.
Figure 32:
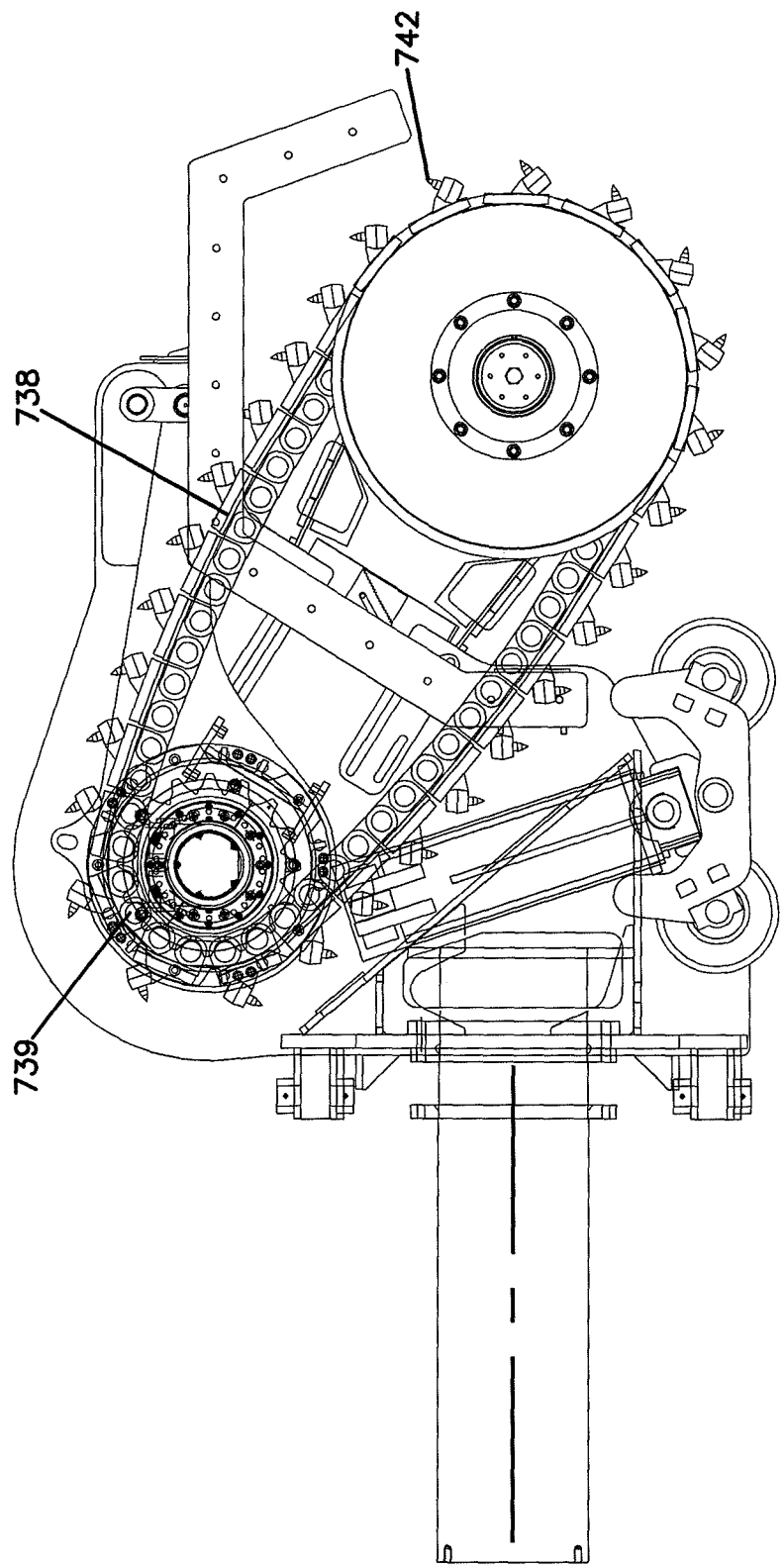
FIG. 32 is a cross sectional view showing an excavation chain utilized by the surface excavation machine of FIG. 31.

FIGS. 31 and 32 show another surface excavation machine 720 suitable for using a reducing element wear sensing system of a type described herein. As compared to utilizing a drum, the surface excavation machine 720 includes reducing elements 742 carried by a chain 738. The chain 738 is driven by a gear 739. By monitoring the speed and rotation of the gear, and by knowing the circumferential length of the chain 738, it is possible to monitor the rotational position of the chain 738 during use. In certain examples, the rotational position of the chain can be identified by sensing reducing elements arranged in a non-repeating configuration along a given reducing path. A non-repeating configuration is a configuration that does not repeat over the course of one full rotation of the chain. The simplest non-repeating configuration is a single reducing element corresponding to one sensor and/or one reducing path. By detecting the presence of the single reducing element and monitoring the speed and rotation of the chain 738, the controller can establish a position of the reducing element on the chain and can determine the rotational position of all the other reducing elements on the chain. Another example of a non-repeating pattern includes two reducing elements monitored on the same reducing path that are not uniformly spaced about the perimeter of the chain.

Figure 33:
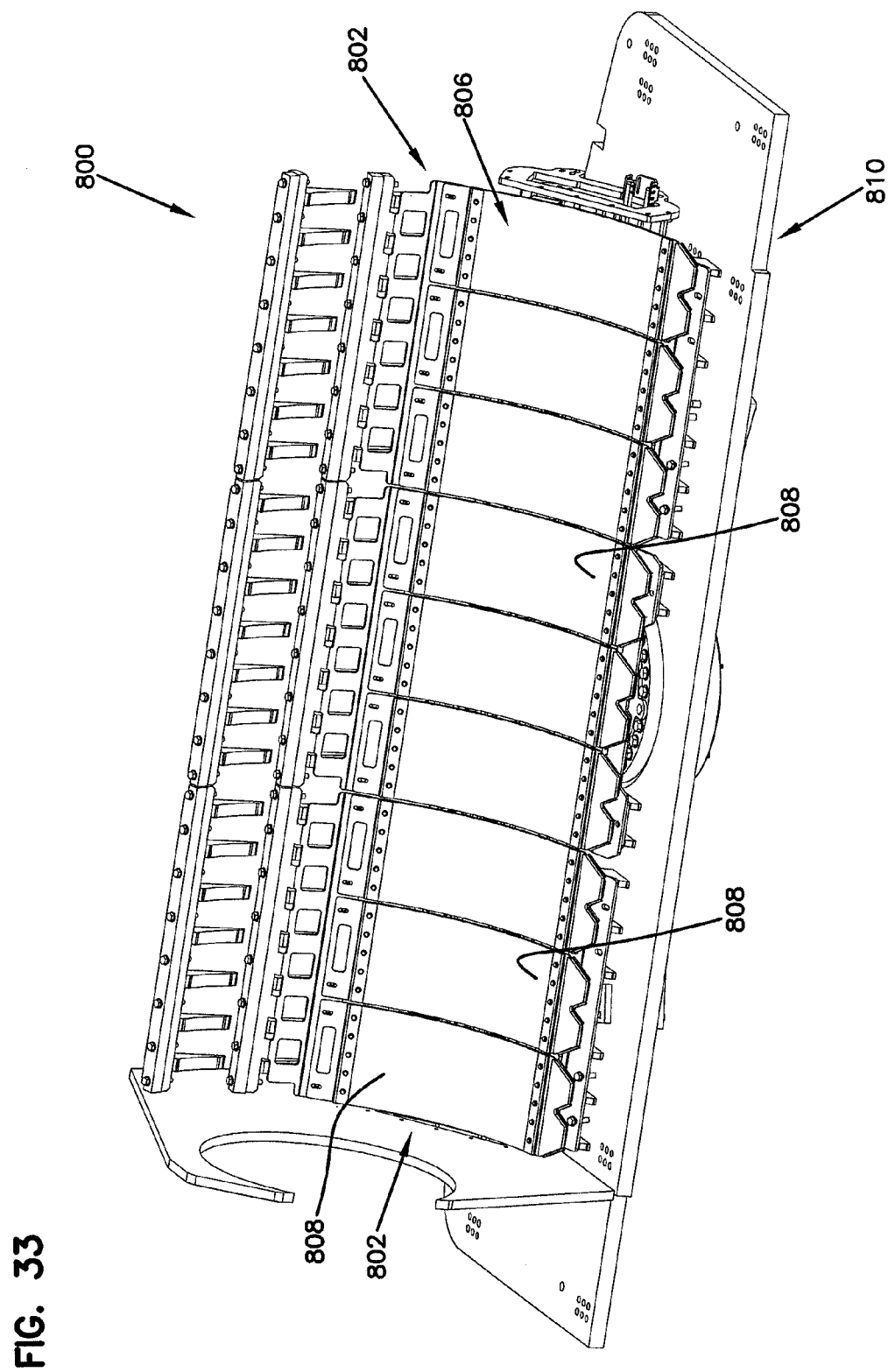
FIG. 33 is another example of a wear sensing system showing a first level of protection in the form of an initial barrier layer in accordance with the principles of the present disclosure.
Figure 34:
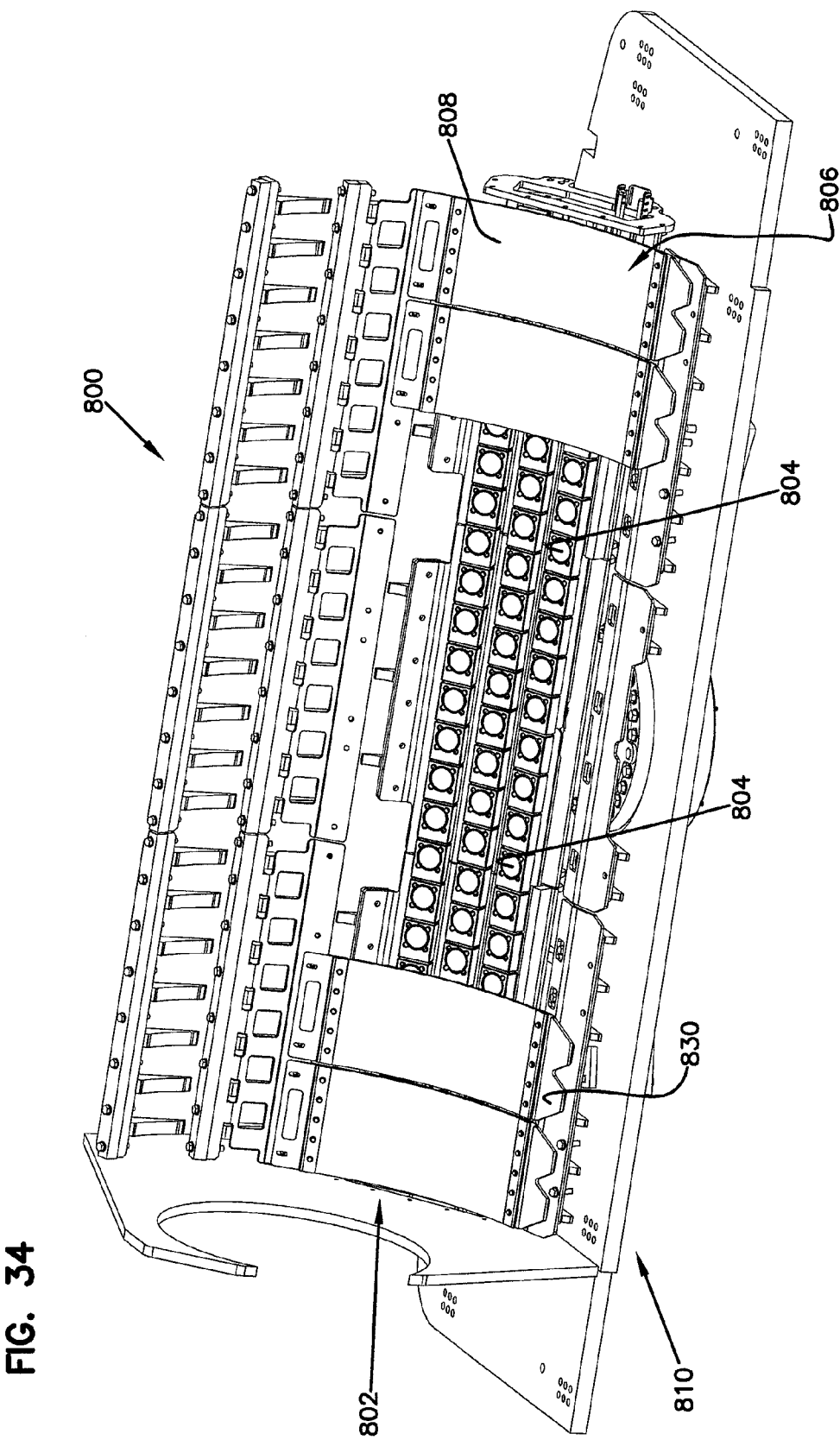
FIG. 34 shows a portion of the initial barrier layer removed.

FIGS. 33 and 34 show another example of a wear sensing system 800 in accordance with the principles of the present disclosure. The wear sensing system 800 can include a multi-level wear sensor protection system 802. The wear sensor protection system 802 is configured to protect wear sensors 804 (see FIG. 34) from damage under the most extreme conditions. The multi-level wear sensor protection system 802 is also configured to allow the wear sensors 804 to provide sensing functionality during milling operations. Thus, the wear sensing system 800 can provide continuous tooth wear monitoring without requiring interruptions in milling operations for assessing tooth wear. The multi-level wear sensor protection system 802 includes a first level of protection, a second level of protection, and a third level of protection. The first level of protection is illustrated and described in more detail in FIG. 35.

The first level of protection can be in the form of an initial barrier layer 806 (e.g., initial shield layer). In one example, the initial barrier layer 806 surrounds the reducing drum (not shown) and is positioned between the reducing drum and the wear sensors 804. In one example, the initial barrier layer 806 curves at least partially around the reducing drum. In one example, the initial barrier layer 806 can have a radius of curvature centered on the axis of rotation of the reducing drum. In certain examples, the initial barrier layer 806 can have a sheet-like construction including a plurality of sheet segments 808 secured to the machine frame 810 in a side-by-side arrangement. In certain examples, the initial barrier layer 806 can include a material such as polycarbonate. In FIG. 34, the initial barrier layer 806 is shown with portions of the plurality of sheet segments 808 removed.

Figure 35:
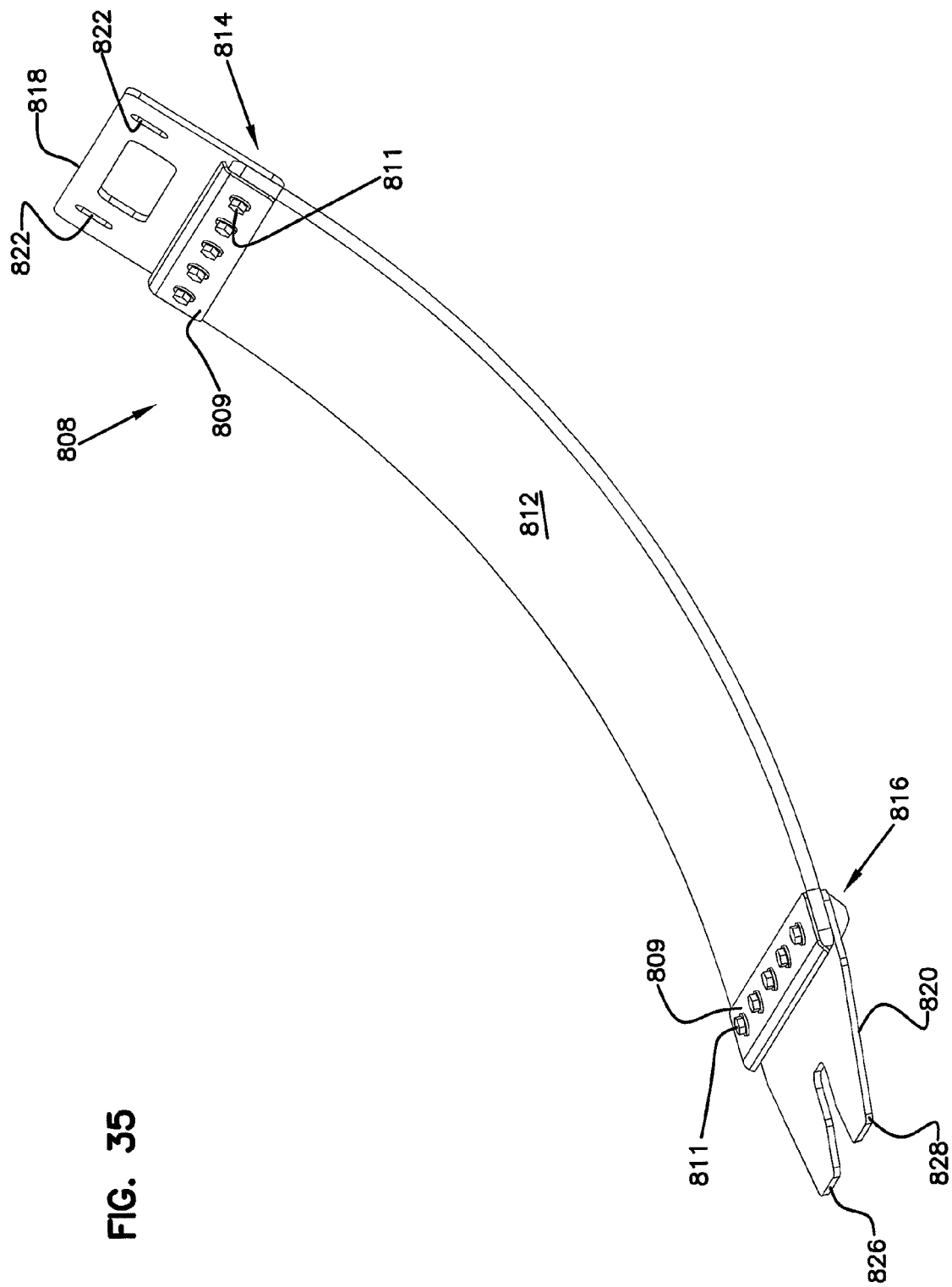
FIG. 35 illustrates one of a plurality of sheet segments of the initial barrier layer with fittings attached.
Figure 36:
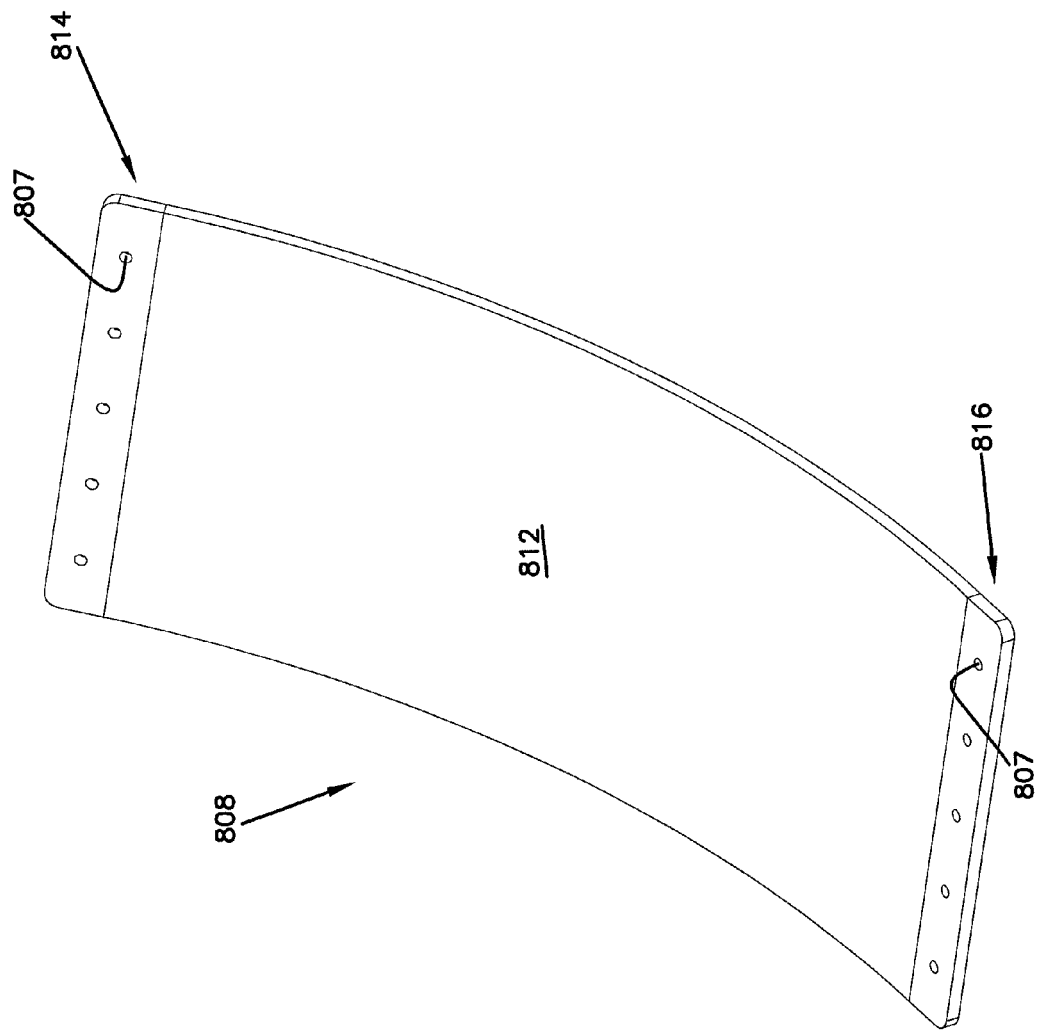
FIG. 36 illustrates one of the plurality of sheet segments without the fittings.

Referring to FIGS. 35-36, one of the plurality of sheet segments 808 is depicted. In the depicted example, the sheet segment 808 includes a main segment body 812 having an upper end 814 and a lower end 816. In certain examples, the upper and lower ends 814, 816 of the main segment body 812 can respectively be secured with upper and lower fittings 818, 820 (e.g., fixtures). The upper fitting 818 can include fastener openings 822 for receiving fasteners (not shown) used to secure the sheet segment 808 to the machine frame 810 (see FIG. 33). The lower fittings 820 can each include a first tab 826 and a second tab 828 that fit within corresponding tab receptacles 830 (see FIG. 34).

In certain examples, the plurality of sheet segments 808 can include openings 807 (see FIG. 36) at the upper and lower ends 814, 816 of the main segment body 812. The plurality of sheet segments 808 can be secured to the fittings 818, 820 using fastening bands 809 that include apertures (not shown) that align or correspond with the openings 807 of the plurality of sheet segments 808. In one example, the fastening bands 809 are attached to the plurality of sheet segments 808 using fasteners 811 (e.g., rivets, cap screw, pins, ties, adhesive, etc.) to secure the plurality of sheet segments 808 to the upper and lower fittings 818, 820 respectively.

The initial barrier layer 806 can have a robust construction. In certain examples, the initial barrier layer 806 can be easily replaced and has a relatively low cost. In certain examples, each of the plurality of sheet segments 808 can be installed by sliding the sheet-like structure downwardly about the rotor along a guide track until the first and second tabs 826, 828 fit within the corresponding tab receptacles 830 secured to the machine frame 810. Thereafter, fasteners can be used to secure the upper ends 814 of the plurality of sheet segments 808 to the machine frame 810.

In certain examples, the upper ends 814 of the plurality of sheet segments 808 are at a location that is easily accessed by an operator. To remove one of the plurality of sheet segments 808 for replacement, the fasteners at the upper ends 814 of each of the plurality of sheet segments 808 are removed and the plurality of sheet segments 808 are slid upwardly to disengage the first and second tabs 826, 828 from the tab receptacles 830 and to slide the plurality of sheet segments 808 out from around the reducing component.

Figure 37:
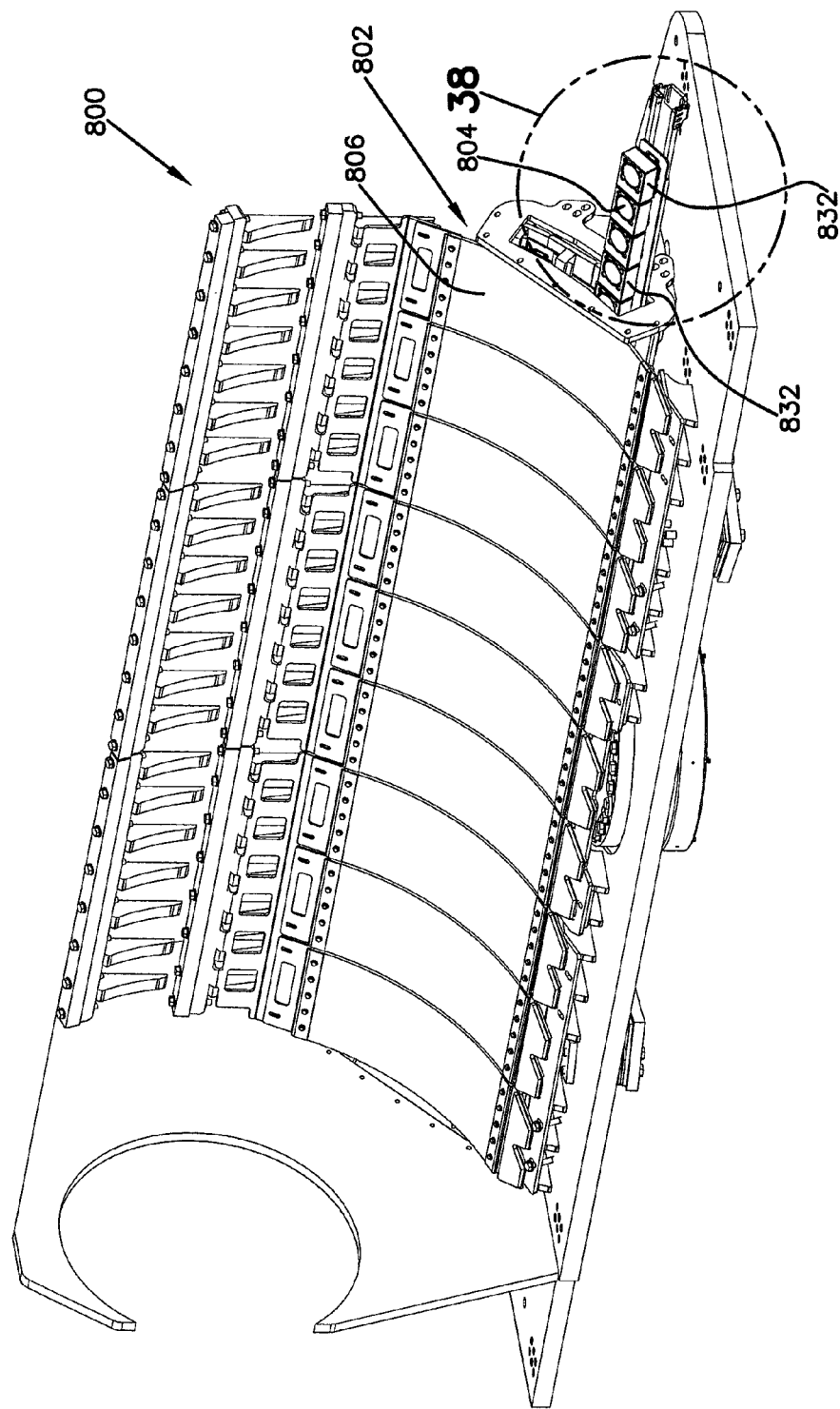
FIG. 37 illustrates the multi-level wear sensor protection system with a second level of protection in the form of trays.

Referring to FIG. 37, the multi-level wear sensor protection system 802 can also include a second level of protection in the form of trays 832 (e.g., housings) 832 in which the wear sensors 804 are mounted. In certain examples, the trays 832 are mounted behind the initial barrier layer 806 and are configured to absorb impacts that are transmitted through the initial barrier layer 806 to prevent the impacts from impacting upon the wear sensors 804 contained within the trays 832. In certain examples, the trays 832 include a wear resistant material such as polycarbonate. The trays 832 help provide impact protection to the wear sensors 804 while concurrently allowing magnetic fields generated by the wear sensors 804 to pass through the trays 832. The second level of protection is illustrated and described in more detail in FIGS. 38-42.

Figure 38:
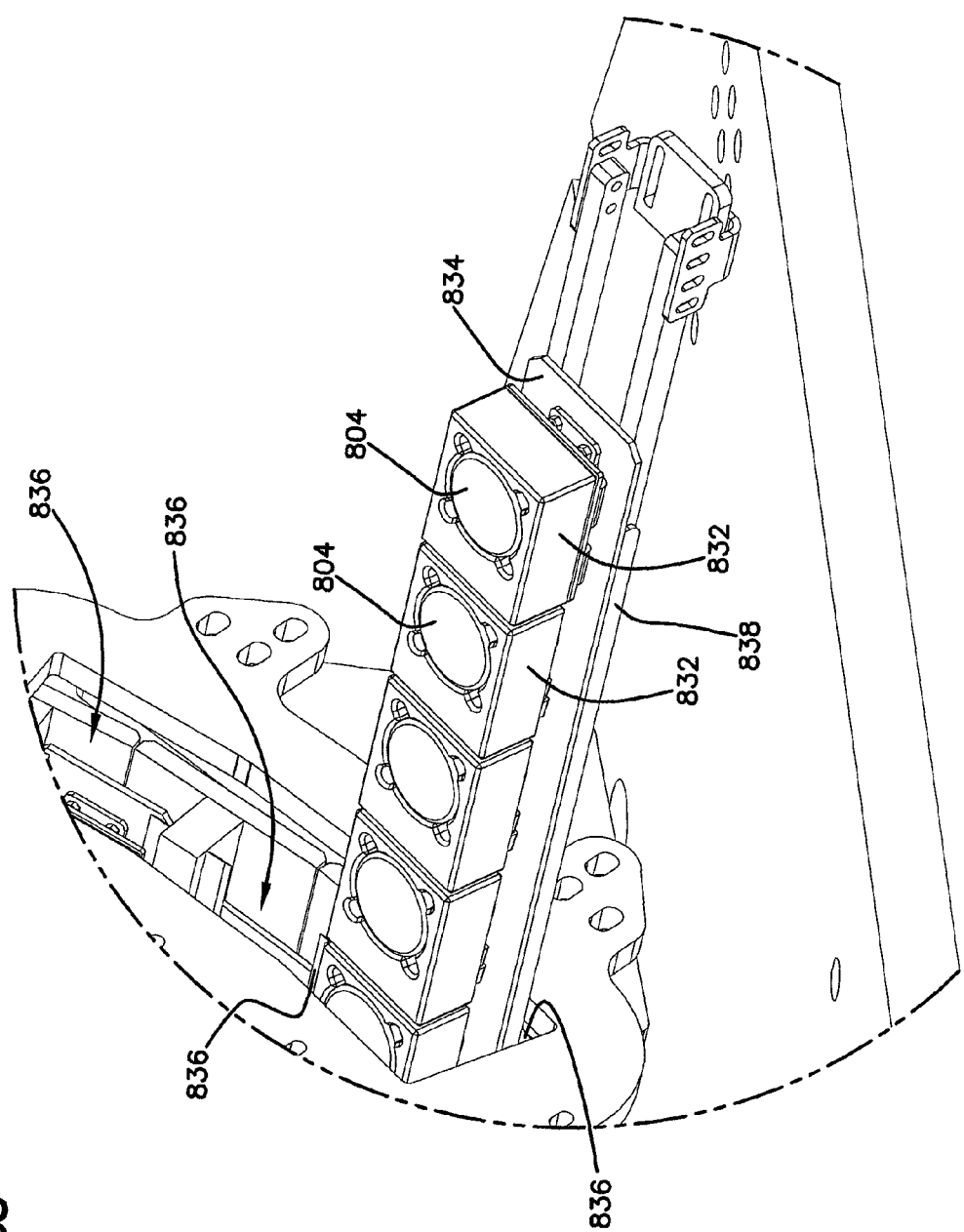
FIG. 38 is an enlarged view of a portion of the second level of protection shown in FIG. 37.
Figure 39:
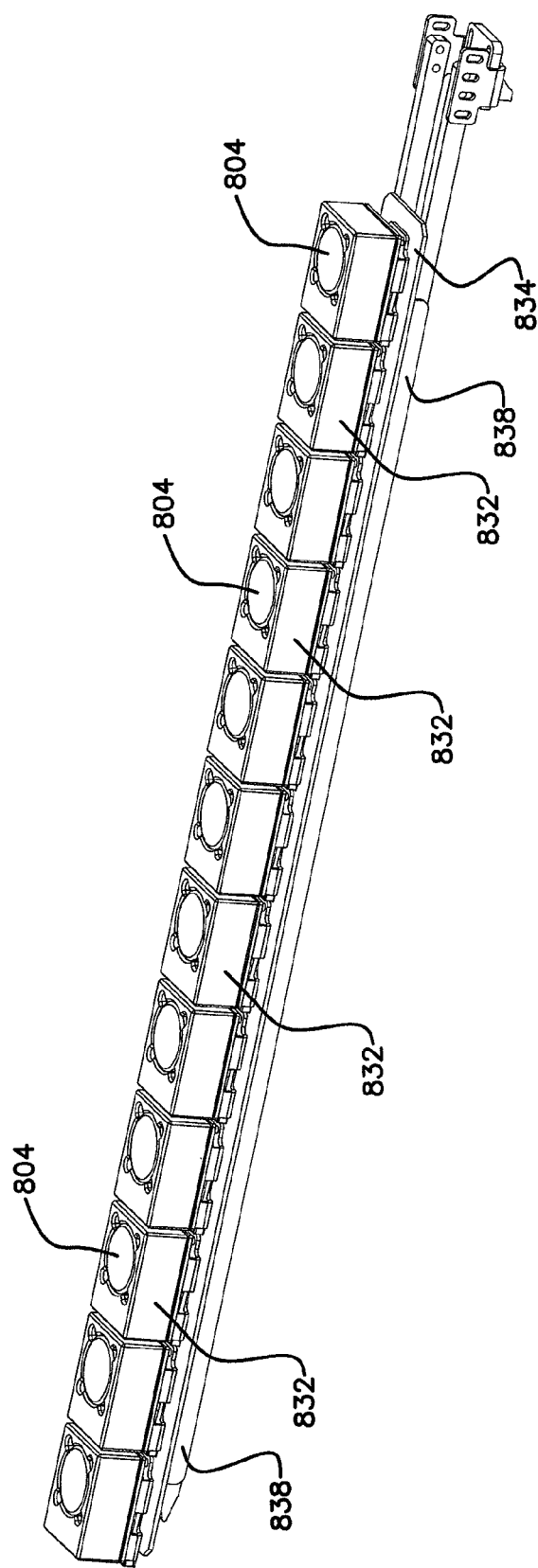
FIG. 39 is a perspective view of the second level of protection with an array of trays as shown in FIG. 37.

Referring to FIGS. 38-39, details of the trays 832 are illustrated. The trays 832 can be configured to hold the wear sensors 804 such that the wear sensors 804 are open-faced within in the trays 832 (i.e., the trays do not cover the major outer faces of the sensors). FIG. 38 is an enlarged view of a portion of the second level of protection shown in FIG. 37. In the depicted example, several trays 832 are shown in a side-by-side arrangement. In one example, the trays 832 can be mounted together along a plate 834. The plate 834 can be arranged and configured to slide a plurality of the trays 832 and wear sensors 804 as a unit into channels 836. As depicted, the channels 836 are constructed to be parallel to one another.

In certain examples, rails 838 can be attached to the plates 834. The rails 838 can have lengths that extend along the drum axis. The rails 838 can be secured (e.g., welded, coupled) to the plate 834 opposite to that of the trays 832. The plate 834 can be slid longitudinally into the channels 836 that extend along the drum axis.

Referring to FIG. 39, an array of trays 832 is depicted along the plate 834. The plate is shown attached to the rails 838. In certain examples, the plate 834 can be inserted in channels 836 from a right side of the machine. It will be appreciated that the plate 834 including the array of trays 832 can also be inserted into channels 836 from a left side of the machine.

Figure 41:
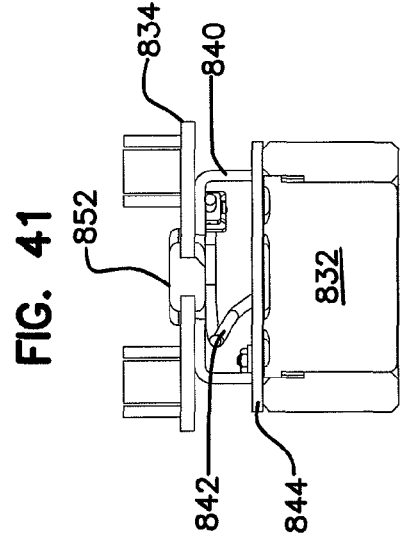
FIG. 41 is a cross-sectional view taken along section line 41-41 of FIG. 40.
Figure 40:
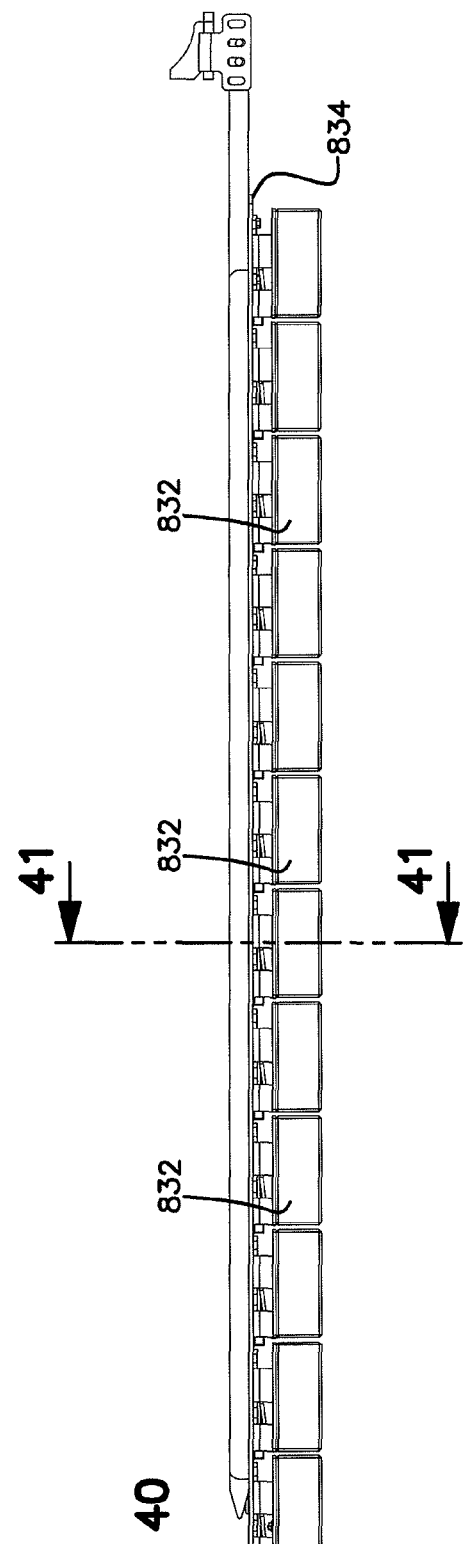
FIG. 40 is a side perspective view of the second level of protection shown in FIG. 37.

Referring to FIG. 40, a side view of the array of trays 832 positioned along the plate 834 is shown. FIG. 41 shows a cross-sectional view of the array of trays 832 shown in FIG. 40.

Referring to FIG. 41, the third level of protection is depicted. The third level of protection includes an impact absorption structure 840 (e.g., relief structure) for accommodating impacts that are transmitted through both the initial barrier layer 806 (see FIG. 37) and the trays 832. In the depicted example, electrical contacts and wiring 842 are shown on a back side of the wear sensor 804 (see FIG. 39) for allowing the wear sensor 804 to be electrically connected to a control system having suitable control circuitry for controlling operation of the wear sensor 804. A metal plate 844 can be mounted to the impact absorption structure 840 adjacent to a back side of the wear sensor 804. The impact absorption structure 840 is illustrated and described in more detail in FIG. 42.

Figure 42:
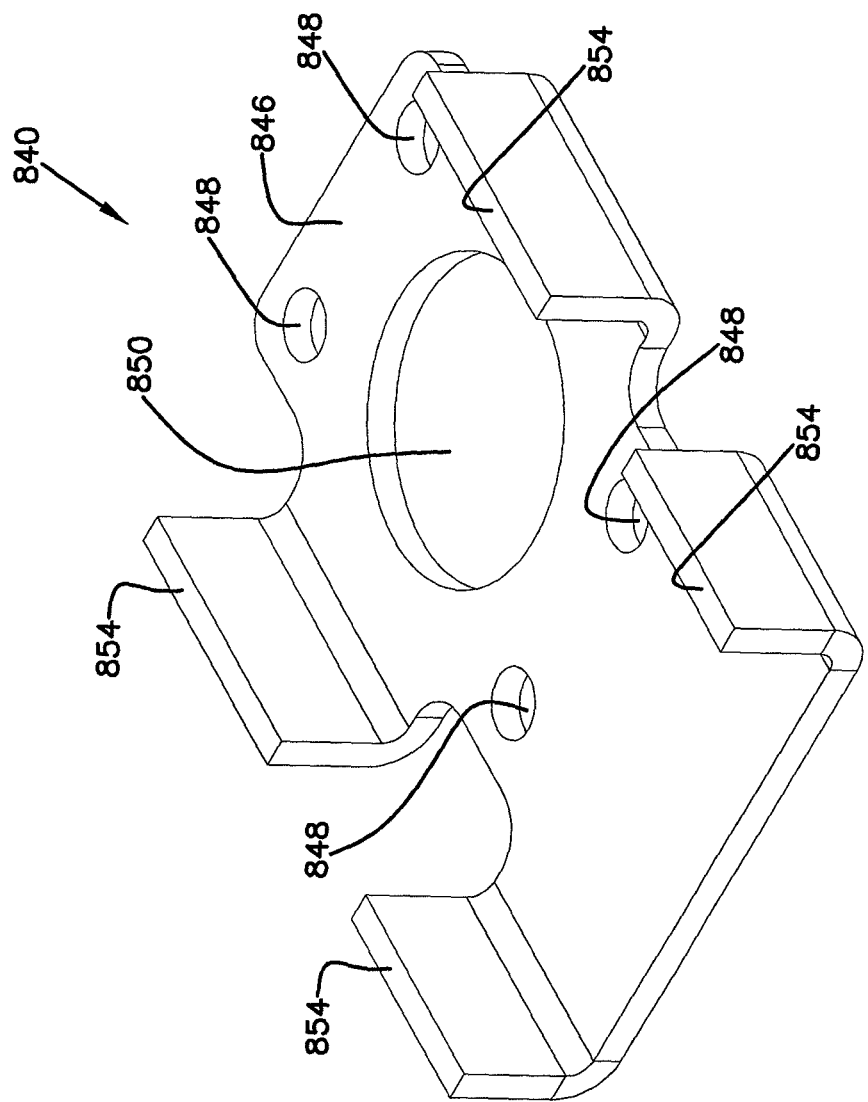
FIG. 42 is a perspective of a third level of protection in the form of an impact absorption structure in accordance with the principles of the present disclosure.

Referring to FIG. 42, an example of the impact absorption structure 840 is illustrated. The impact absorption structure 840 includes a base 846 that can be attached to the plate 834 (see FIG. 41). The base 846 can define a plurality of apertures 848 for receiving fasteners (not shown) to couple the impact absorption structure 840 to the plate 834. In certain examples, the base 846 of the impact absorption structure 840 can define a center opening 850. The center opening 850 can be configured to receive a grommet 852 (see FIG. 41). In certain examples, the impact absorption structure 840 can be arranged and configured to bend and flex about legs 854 upon impact.

Figure 43:
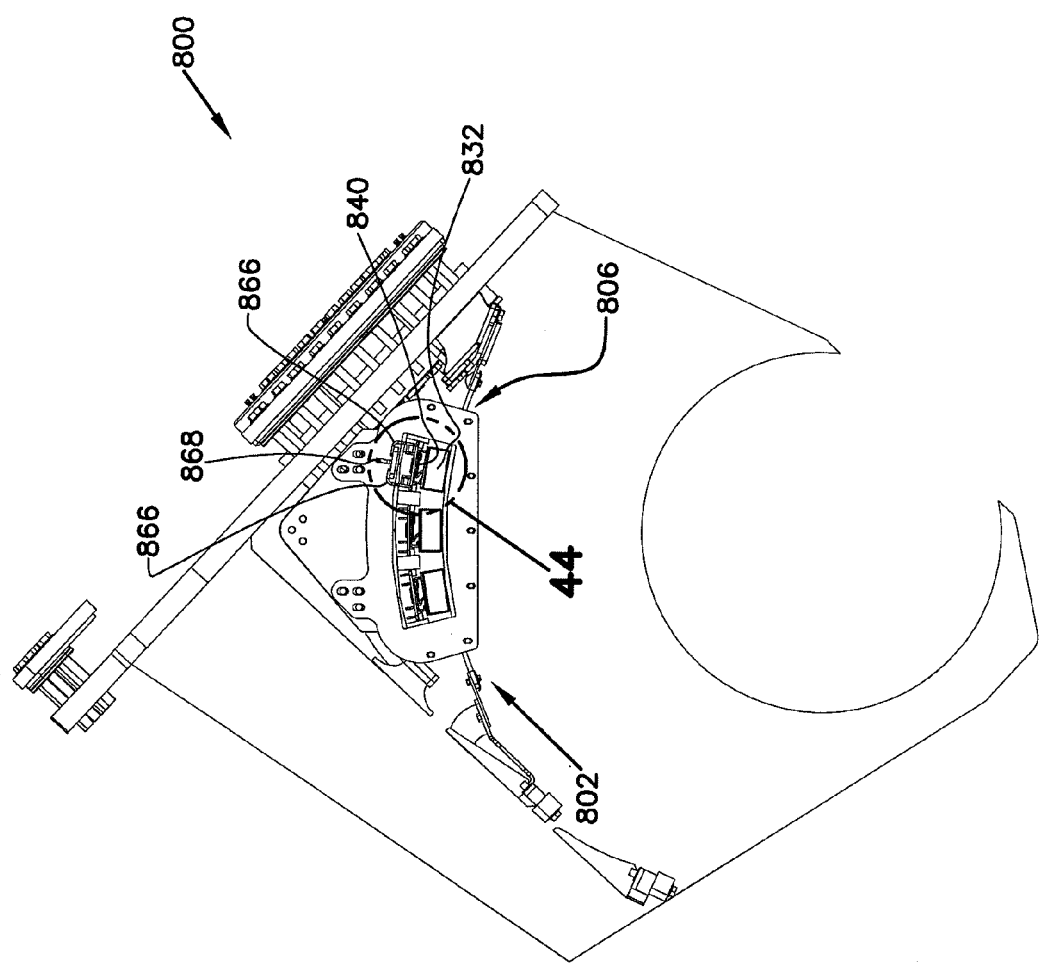
FIG. 43 is a side view depicting the third level of protection.
Figure 44:
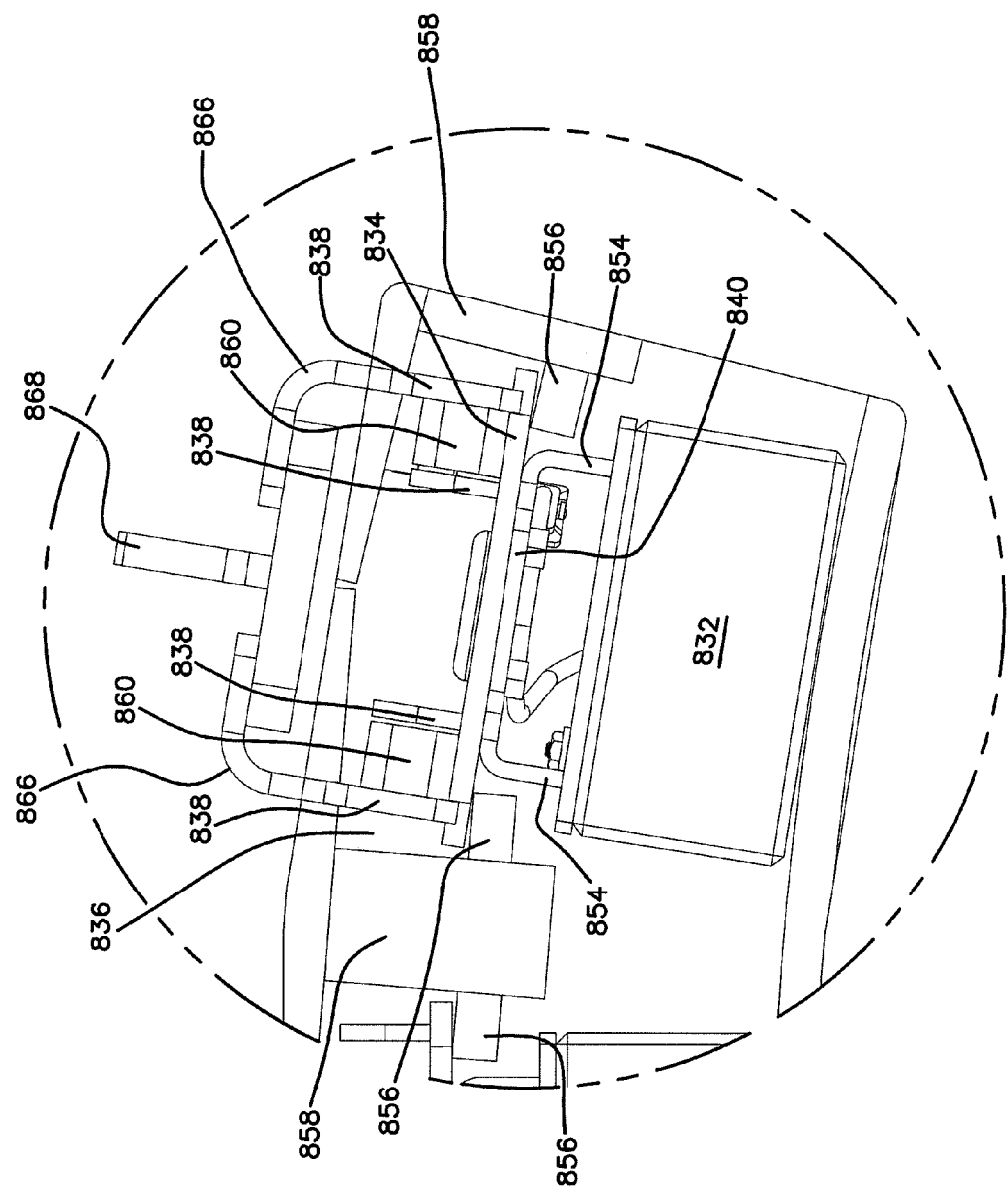
FIG. 44 is an enlarged view of a portion of FIG. 43.

Referring to FIG. 43, a side perspective view of the third level of protection is shown. FIG. 44 is an enlarged view of a portion of FIG. 43. In FIG. 44, the impact absorption structure 840 (e.g., relief structure) can be positioned behind the trays 832 to help accommodate movement of the trays 832 in response to an impact that passes through the initial barrier layer 806 (see FIG. 37) and upon the trays 832. The legs 854 of the impact absorption structure 840 are configured to bend upon impact.

In some examples, the impact absorption structure 840 can include a structure that in-elastically deforms in response to an impact. In such situations, the impact absorption structure 840 will remain bent upon impact. It will be appreciated that such structures would likely require fixing or replacement more often than a resilient structure. In other examples, the impact absorption structure 840 can be made of a plastic material for providing flexibility upon impact such that the impact absorption structure 840 does not remain bent upon impact.

In certain examples, the impact absorption structure 840 can include an elastic/resilient structure that biases the trays 832 toward a sensing position and allows the trays 832 to move away from a reducing component in response to an impact. After impact, such resilient impact absorption structures 840 can bias the impacted trays 832 back toward their corresponding sensing positions. The third level of protection is illustrated and described in more detail in FIGS. 44-48.

Referring still to FIG. 44, the legs 854 of the impact absorption structure 840 can be coupled to the trays 832 to secure the trays 832 along the plate 834. The plate 834 having the impact absorption structure 840 mounted thereon is shown positioned within the channel 836.

Figure 45:
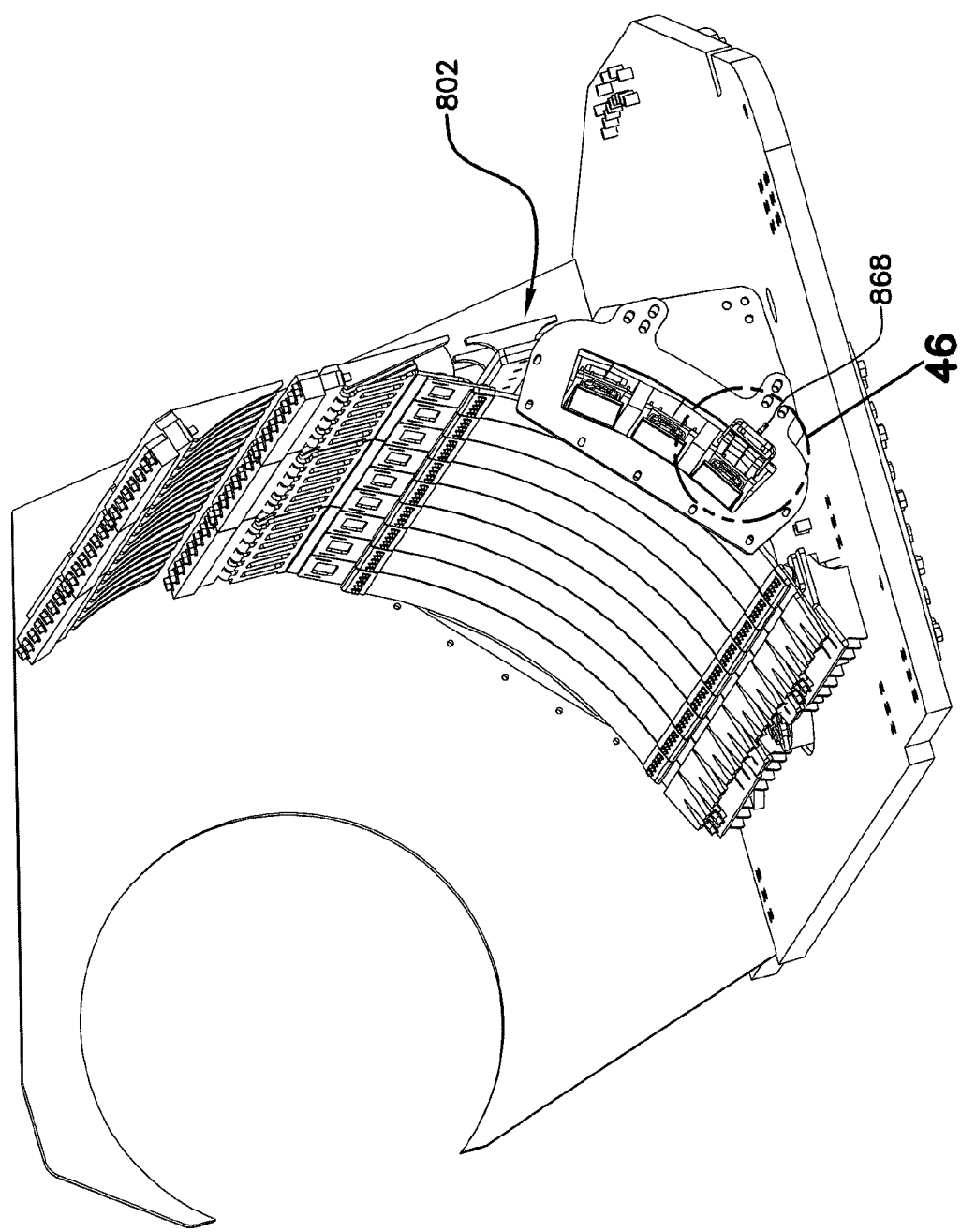
FIG. 45 is another perspective view of the multi-layer wear sensor protection system.

Referring to FIG. 45, a bottom view of the multi-layer wear sensor protection system 802 is shown. Details of the construction of the multi-layer wear sensor protection system is illustrated and described in more detail in FIG. 46.

Figure 46:
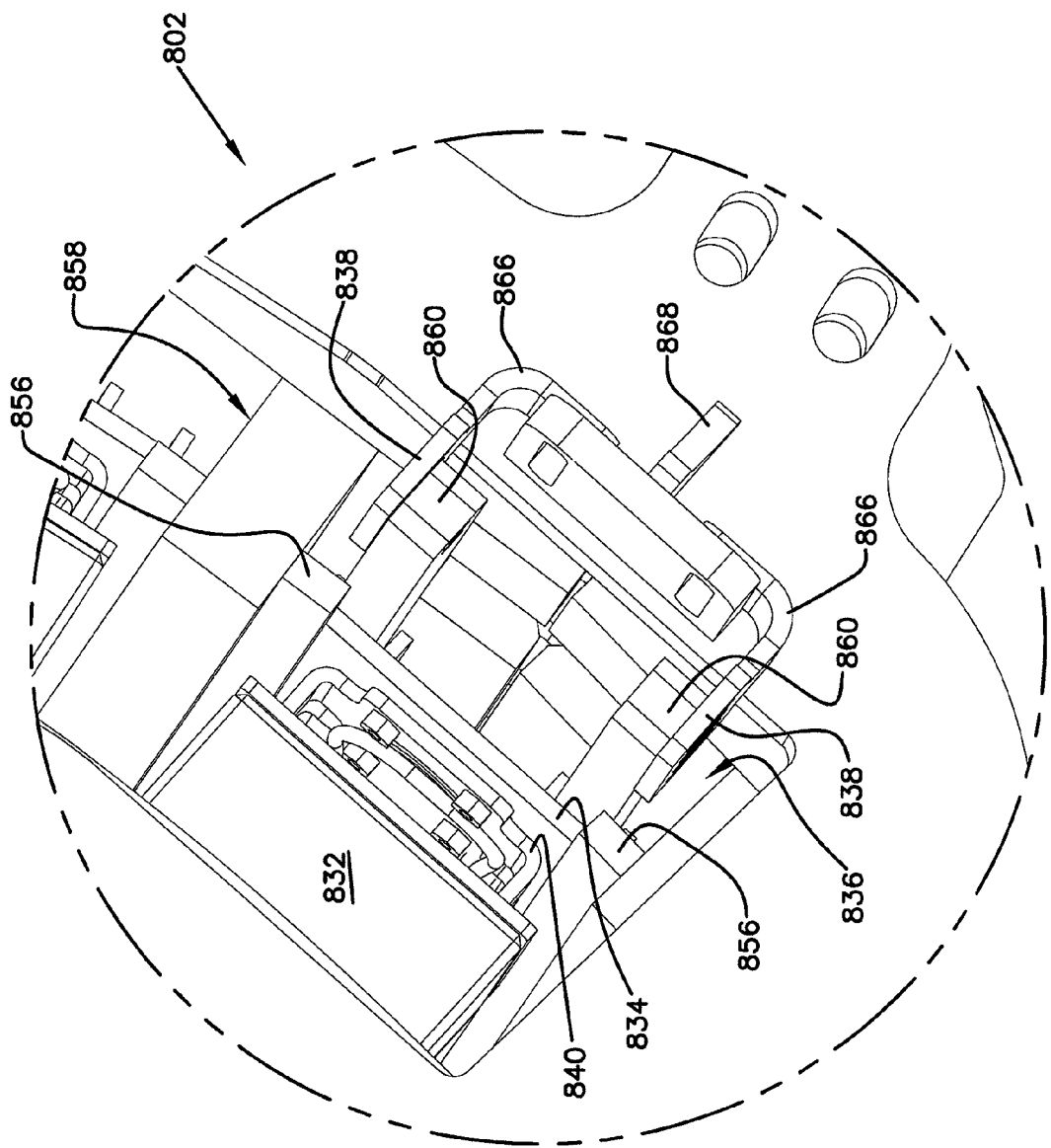
FIG. 46 is an enlarged view of a portion of FIG. 45.

In FIG. 46, an enlarged view of a portion of FIG. 45 is shown. The construction of the multi-level wear sensor protection system 802 allows for a unit of trays 832 secured to the impact absorption structure 840 to be inserted into the channels 836 from either a left or right side of the machine by the plate 834.

Referring again to FIGS. 44 and 46, the plate 834 can slide into the channels 836 on top of ledges 856. In certain examples, the ledges 856 can be welded to elongated members 858 that extend longitudinally along the drum axis. In one example, the rails 838 (see FIG. 40) located within the channels 836 can receive wedges 860.

Figure 49:
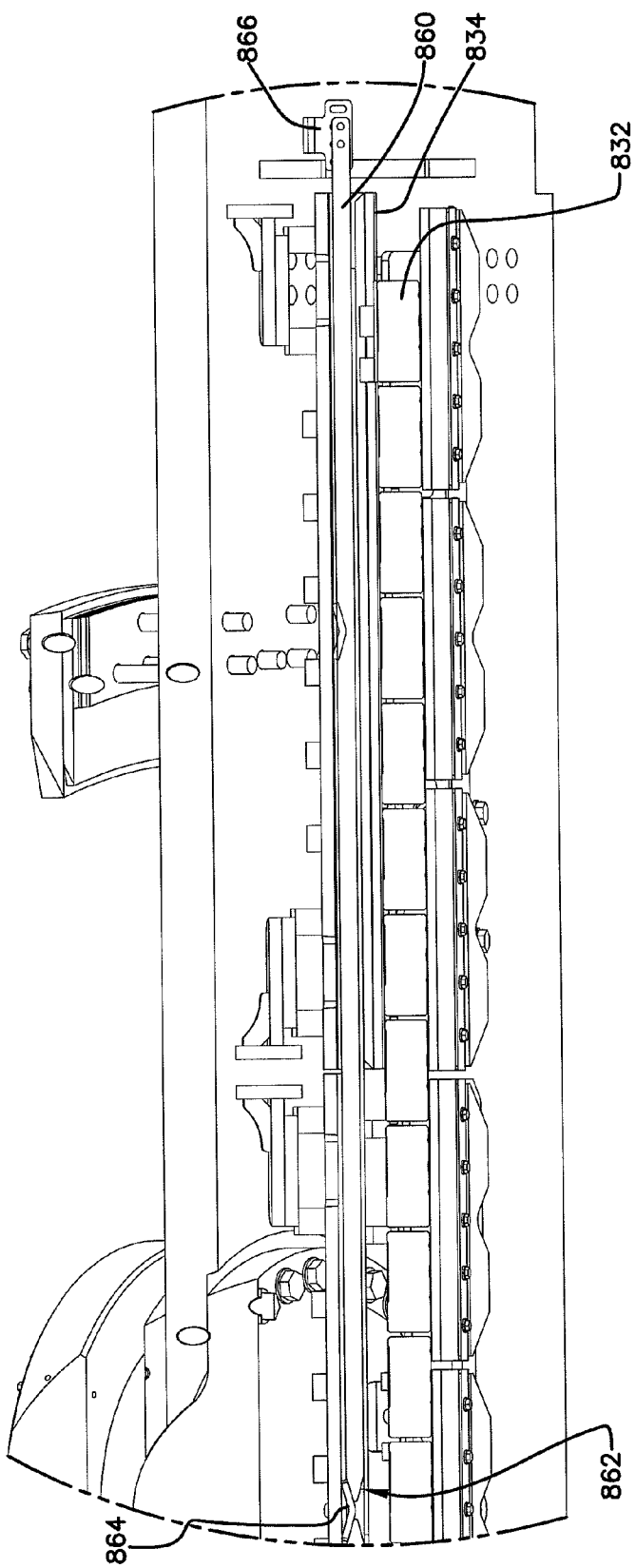
FIG. 49 is an enlarged view of a portion of FIG. 48.

Referring to FIG. 47, a side view of the multi-layer wear sensor protection system 802 is shown. FIG. 48 is a cross-sectional view of the multi-layer wear sensor protection system 802 illustrating the array of trays 832 in the channel 836 along the drum axis. FIG. 49 is an enlarged view of a portion of FIG. 48.

Referring to FIG. 49, the wedges 860 can include a tapered end 862. In one example, the wedges 860 can be inserted along the rails 838 (see FIG. 46) from the left and/or right sides of the machine. Thus, the rails 838 can guide the wedges 860 during insertion. The wedges 860 can be inserted such that the tapered end 862 of the wedges 860 engage a ramp surface 864 in a center portion of the channel 836 when fully inserted.

In one example, the wedges 860 provide downward force to the plate 834 to clamp down on the trays 832 to provide stability and keep the plate 834 in place. For example, the plates 834 are clamped against the ledges 856. In certain examples, the wedges 860 can be coupled to L-shaped brackets 866 to keep the wedges 860 in position. In one example, the wedges 860 can be bolted to the L-shaped brackets 866. The L-shaped bracket 866 can be attached to the main bracket 868 (see FIG. 47) and can be moved relative to the main frame via fasteners to control the position of the outer ends (i.e., the non-tapered ends) of the wedges 860 to ensure the plate 834 is firmly clamped against the ledges/shoulders 856 of the channels 836 along its entire length.

From the forgoing detailed description, it will be evident that modifications and variations can be made without departing from the spirit and scope of the disclosure.

What is claimed is:

1. A material reducing machine including wear sensing, the material reducing machine including:
 a rotatable reducing structure including a carrier and a plurality of reducing elements carried by the carrier; and
 a wear sensing system including a sensor that senses a general wear state of at least one of the reducing elements by sensing a general physical characteristic of the reducing element without measuring a position of a specific point on the rotatable reducing structure;
 wherein the sensor is an inductive sensor, and wherein the wear sensing system can sense the general physical characteristic of the reducing element when the material reducing machine is performing a reducing operation without contacting the reducing element.

2. The material reducing machine of claim 1, wherein the rotatable reducing structure is at least partially covered by a shroud, wherein the sensor is mounted inside the shroud adjacent to the rotatable reducing structure, and wherein the material reducing machine further comprises a breaker structure positioned within the shroud upstream from the sensor, the breaker structure being spaced a first distance from a reducing boundary of the rotatable reducing structure and the sensor being spaced a second distance from the reducing boundary of the rotatable reducing structure, the second distance being longer than the first distance.

3. The material reducing machine of claim 2, wherein the breaker structure includes first and second breaker bar structures, the first breaker bar structure being upstream from the second breaker bar structure.

4. The material reducing machine of claim 1, wherein the wear sensing system includes a plurality of the sensors and a plurality of protective housings within which the sensors are mounted, wherein the wear sensing system includes a plurality of the rows of the protective housings that extend along the axis of rotation of the rotatable reducing structure, and wherein the sensors of adjacent rows are staggered.

5. The material reducing machine of claim 1, wherein the sensor includes a plurality of inductive sensors, and wherein the inductive sensors are housed within trays with each tray having an open front face that does not cover a major face of its corresponding inductive sensor.

6. The material reducing machine of claim 1, wherein the reducing elements define a plurality of reducing paths, wherein the wear sensing system includes a plurality of the sensors, wherein the sensors are inductive sensors, wherein the material reducing machine includes a shroud covering at least a portion of the rotatable reducing structure, wherein the inductive sensors are positioned within the shroud for sensing the reducing elements, and wherein the inductive sensors are arranged such that each of the reducing paths is assigned a corresponding one of the inductive sensors.

7. The material reducing machine of claim 6, wherein the inductive sensors are arranged in a multi-row array.

8. The material reducing machine of claim 1, wherein the reducing elements define a plurality of reducing paths, wherein the wear sensing system includes a plurality of the sensors, wherein the sensors are inductive sensors, wherein the material reducing machine includes a shroud covering at least a portion of the rotatable reducing structure, wherein the inductive sensors are positioned within the shroud for sensing the reducing elements, and wherein the inductive sensors each have an effective sensing distance, the inductive sensors also having a center-to-center spacing measured along the axis of rotation, the inductive sensors being arranged such that the center-to-center spacing is smaller than the effective sensing distance.

9. The material reducing machine of claim 1, wherein the reducing elements define a plurality of reducing paths, wherein the wear sensing system includes a plurality of the sensors, wherein the sensors are inductive sensors, wherein the material reducing machine includes a shroud covering at least a portion of the rotatable reducing structure, wherein the inductive sensors are positioned within the shroud for sensing the reducing element, the inductive sensors including first and second inductive sensors having overlapping electromagnetic field boundaries, and the material reducing machine including a controller that operates the wear sensing system in a first sensing phase in which the first inductive sensor is energized and the second inductive sensor is de-energized, and that also operates the wear sensing system in a second sensing phase in which the first inductive sensor is de-energized and the second inductive sensor is energized.

10. The material reducing machine of claim 1, wherein the reducing elements define a plurality of reducing paths, wherein the wear sensing system includes a plurality of the sensors, wherein the sensors are inductive sensors, wherein the material reducing machine includes a shroud covering at least a portion of the rotatable reducing structure, wherein the inductive sensors are positioned within the shroud for sensing the reducing element, the inductive sensors including first and second sets of inductive sensors, the inductive sensors of the first set having non-overlapping electromagnetic field boundaries and the sensors of the second set having non-overlapping electromagnetic field boundaries, the electromagnetic field boundaries of the first set overlapping the electromagnetic field boundaries of the second set, and the material reducing machine including a controller that operates the wear sensing system in a first sensing phase in which the first set of inductive sensors is energized and the second set of inductive sensors is de-energized, and that also operates the wear sensing system in a second sensing phase in which the first set of inductive sensors is de-energized and the second set of inductive sensors is energized.

11. The material reducing machine of claim 1, wherein the reducing elements define a plurality of reducing paths, wherein the wear sensing system includes a plurality of the sensors, wherein the sensors are inductive sensors, wherein the material reducing machine includes a shroud covering at least a portion of the rotatable reducing structure, wherein the inductive sensors are positioned within the shroud for sensing the reducing element, and the material reducing machine includes a controller that operates the wear sensing system and processes base-line and real-time wear readings from the inductive sensors to determine the wear states of the reducing elements, wherein processing the base-line and real-time wear readings includes compensating for temperature variations.

12. The material reducing machine of claim 1, wherein the reducing elements define a plurality of reducing paths, wherein the wear sensing system includes a plurality of the sensors, wherein the sensors are inductive sensors, wherein the material reducing machine includes a shroud covering at least a portion of the rotatable reducing structure, wherein the inductive sensors are positioned within the shroud for sensing the reducing element, and the material reducing machine includes a controller that operates the wear sensing system and processes base-line and real-time wear readings from the inductive sensors to determine the wear states of the reducing elements, wherein processing the base-line and real-time wear readings includes compensating for variations in a rotational speed of the rotatable reducing structure.

13. The material reducing machine of claim 1, wherein the reducing elements define a plurality of reducing paths, wherein the wear sensing system includes a plurality of the sensors, wherein the sensors are inductive sensors, wherein the material reducing machine includes a shroud covering at least a portion of the rotatable reducing structure, wherein the inductive sensors are positioned within the shroud for sensing the reducing element, and the material reducing machine includes a controller that determines a rotational position of the rotatable reducing structure by sensing a non-repeating reducing element configuration corresponding to at least one of the reducing paths.

14. The material reducing machine of claim 1, wherein the reducing elements define a plurality of reducing paths, wherein the wear sensing system includes a plurality of the sensors, wherein the sensors are inductive sensors, wherein the material reducing machine includes a shroud covering at least a portion of the rotatable reducing structure, wherein the inductive sensors are positioned within the shroud for sensing the reducing element, wherein the wear sensing system includes a wear sensor protection system including a first level of protection, a second level of protection, and a third level of protection; wherein the first level of protection includes an initial barrier layer, the initial barrier layer comprising a plurality of sheet segments; wherein the second level of protection includes a side-by-side arrangement of trays positioned behind the initial barrier layer, the trays being configured to absorb impacts that are transmitted through the initial barrier layer to prevent the impacts from impacting upon the sensors, the trays holding the inductive sensors; and wherein the third level of protection includes a relief structure for accommodating impacts that are transmitted through both the initial barrier layer and the trays, the relief structure being positioned behind the trays for accommodating movement of the trays in response to an impact that passes through the initial barrier layer and the trays.

15. The material reducing machine of claim 1, wherein the material reducing machine is a surface excavation machine.

16. The material reducing machine of claim 1, wherein the sensor is mounted adjacent to the rotatable reducing structure.

* * * * *

UNITED STATES PATENT AND TRADEMARK OFFICE
CERTIFICATE OF CORRECTION

PATENT NO. : 9,890,504 B2
APPLICATION NO. : 14/651951
DATED : February 13, 2018
INVENTOR(S) : Stock et al.

Page 1 of 1

It is certified that error appears in the above-identified patent and that said Letters Patent is hereby corrected as shown below:

On the Title Page

(71) Applicants: "Ty Hartwick, Pella, OH (US)" should read --Ty Hartwick, Pella, IA (US)--

(72) Inventors: "Ty Hartwick, Pella, OH (US)" should read --Ty Hartwick, Pella, IA (US)--

Signed and Sealed this
Nineteenth Day of March, 2019

Andrei Iancu
*Director of the United States Patent and Trademark Office*